(12) United States Patent
Rieder et al.

(10) Patent No.: US 8,364,409 B2
(45) Date of Patent: Jan. 29, 2013

(54) METHOD AND COMPOSITION FOR RAPID VIABILITY TESTING OF CELLS

(75) Inventors: Ronald J. Rieder, Medford, MA (US); Boris A. Zavizion, Chestnut Hill, MA (US)

(73) Assignee: Biosense Technologies, Inc., Woburn, MA (US)

( * ) Notice: Subject to any disclaimer, the term of this patent is extended or adjusted under 35 U.S.C. 154(b) by 898 days.

(21) Appl. No.: 11/664,325

(22) PCT Filed: Jan. 11, 2007

(86) PCT No.: PCT/US2007/000682
§ 371 (c)(1),
(2), (4) Date: Mar. 29, 2007

(87) PCT Pub. No.: WO2008/042003
PCT Pub. Date: Apr. 10, 2008

(65) Prior Publication Data
US 2009/0197243 A1 Aug. 6, 2009

Related U.S. Application Data

(60) Provisional application No. 60/758,362, filed on Jan. 12, 2006.

(51) Int. Cl.
*C12Q 1/70* (2006.01)
*G01N 33/48* (2006.01)
*G01N 27/02* (2006.01)

(52) U.S. Cl. ............................ 702/19; 73/335.03; 435/5

(58) Field of Classification Search .................. None
See application file for complete search history.

(56) References Cited

U.S. PATENT DOCUMENTS

| | | | | |
|---|---|---|---|---|
| 4,313,929 A * | 2/1982 | Morita et al. | ................. | 436/531 |
| 5,591,599 A | 1/1997 | Chang et al. | ................... | 435/32 |
| 6,031,367 A | 2/2000 | Mangan | ...................... | 324/71.4 |
| 6,051,422 A * | 4/2000 | Kovacs et al. | .............. | 435/287.1 |
| 6,604,225 B1 * | 8/2003 | Otsu et al. | ..................... | 716/136 |
| 7,306,924 B2 * | 12/2007 | Gomez et al. | ................... | 435/7.2 |
| 2002/0086277 A1 | 7/2002 | Chang et al. | ...................... | 435/4 |
| 2005/0059105 A1 * | 3/2005 | Alocilja et al. | ............. | 435/7.32 |
| 2005/0142537 A1 * | 6/2005 | Rieder et al. | ....................... | 435/5 |
| 2005/0208592 A1 * | 9/2005 | Caron et al. | .................. | 435/7.1 |
| 2005/0211559 A1 | 9/2005 | Kayyem | ...................... | 204/601 |

FOREIGN PATENT DOCUMENTS

EP A-1 764 417 3/2007

OTHER PUBLICATIONS

International Search Report & Written Opinion of ISA—dated May 29, 2008, for PCT/US2007/00682, 11 pages (in English).
International Preliminary Report on Patentability—mailed Jul. 31, 2008, for PCT/US2007/00682, 9 pages (in English).
European Search Report—dated Feb. 9, 2009 for EP App. No. 07 861 206.6, 12 pgs (in English).
European Examination Report—dated May 14, 2009 for EP App. No. 07 861 206.6, 5 pgs.
Xiao, C. et al., "Assessment of cytotoxicity by emerging impedance spectroscopy," *Toxicology and Applied Pharmacology*, Academic Press, 206(2): 102-112, XP004964678 ISSN: 0041-008X, Aug. 7, 2005.
McCoy, et al., "Use of electric cell-substrate impedance sensing as a tool for quantifying cytopathic effect in influenza A virus infected MDCK cells in real-time," *Journal of Virological Methods*, Elsevier BV,NL, 130(1-2): 157-161, XP005150575 ISSN:0166-0934, Dec. 1, 2005.

* cited by examiner

*Primary Examiner* — Anna Skibinsky
(74) *Attorney, Agent, or Firm* — Arendt & Associates IP Group; Jacqueline M. Arendt; Richard W. Wagner

(57) ABSTRACT

The present invention relates to a method for rapidly monitoring a stress response of a cell to a stressor and determining the magnitude of the stress response; a method for rapidly detecting the presence or absence of a cell by monitoring a stress response of the cell if said cell is present, or the absence of the stress response if said cell is absent or dead; and a method for determining a predictive outcome for the susceptibility of a cell to a selected concentration of a bio-active agent or environmental factor and a level of stress of the cell at the selected concentration of the bio-active agent. Also disclosed are kits for carrying out the methodology according to an embodiment of the invention.

22 Claims, 10 Drawing Sheets

METHOD AND COMPOSITION FOR RAPID VIABILITY TESTING OF CELLS

This application claims the benefit of U.S. Provisional Application No. 60/758,362 filed on 12 Jan. 2006, the teachings of which are incorporated herein by reference in their entirety.

BACKGROUND OF THE INVENTION

Microbial contamination and infection is one of the greatest challenges to the survival and well-being of humans and animals, and as such continues to consume huge societal resources. An essential component of the effort to combat pathogens is assessing the presence and viability of prokaryotic and eukaryotic cells. Most commercially available methods capable of assessing cell viability routinely rely on cell growth to make this determination. However, a continuing limitation of these conventional approaches is their dependence on the doubling time of the cell population as well as the practical availability of the proper culturing conditions. Especially in the case of slow-growing cells, methods based on biological growth in order to detect observable changes can require significant time. Therefore, existing methods can be ineffective for applications wherein time delays translate into economic costs and, in extreme cases, human lives. Even where existing detection methods are sufficient, more rapid detection could provide increased efficiencies and reduced costs.

Increasing antibiotic resistance of pathogens has led to a global public health problem manifested in untreatable infections in the human population generally, and on farms. Although the problem is complex, it is known that the increasing use of antibiotics has created selective evolutionary pressures wherein many species of bacteria and infectious protozoa have developed resistance mechanisms, making the antibiotics often prescribed to treat disease no longer effective, and resulting in the spreading of bacterial strains resistant to antibiotics.

A majority of existing methods for determining the antibiotic susceptibility of a pathogen also rely on detection of growth, and rely exclusively on biomass increase due to continuous cell division of the pathogen in culture. Standard plating methods can require many days or even weeks, in the case of slow-growing pathogen, to yield drug-susceptibility results. Optical detection methods, while less time-consuming, still require significant time for the cells to grow to a detectable level. Time delays in obtaining susceptibility test results have led to the clinical practice of empirically prescribing therapies to treat life-threatening infections. The inability to identify antimicrobial-resistant cells in a timely manner results in the prescription of inappropriate therapies and consequently, unfavorable patient outcomes. The continuing emergence of drug resistant strains threatens our ability to treat life-threatening infections through a growing use of ineffective drugs.

There is an ongoing need to reduce the indiscriminate and non-essential use of antibiotics in order to significantly improve patient outcomes and also reduce the spread of bacteria resistant to antibiotics. The disclosed invention provides a means for identifying antibiotic-resistant pathogens rapidly, thereby reducing the number of unnecessarily-prescribed antibiotics.

The ability to detect the presence of harmful cells rapidly and reliably is important for the safe use of numerous medical and industrial products, and the safe and efficient implementation of medical procedures and industrial processes. Rapid determination of water quality during emergency situations, such as floods and earthquakes, immediate diagnosis of trauma patients, screening of raw materials/process equipment in the food industry, monitoring of quality during the pharmaceutical manufacturing phases, and monitoring of biologics and fermentation processes are only a few examples of the applications for the disclosed invention.

Another on-going problem relates to the fact that a functional shelf-life of a unit of platelets, a blood product transfused to control bleeding, is only five days. In order to preserve their physiological function, the platelets must be stored at room temperature. Such conditions are favorable for the growth of many contaminant species of bacteria in the stored units. If not detected, this growth could lead to post-transfusion infection and septic reactions. Methods currently used to establish the sterility of these products require 48 hours time for fast-growing cells, and significantly longer for slow-growing cells in order to grow the cells to detectable levels. Consequently, the effective lifespan of a unit of platelets is reduced to only three days. A more rapid method for identifying fast- and slow-growing contaminant bacteria growing in platelets would increase the useful lifespan of the platelets and place less pressure on an already precious resource.

Bacterial meningitis is an infection causing inflammation of the meninges. In order to recognize bacterial cases wherein a delay in beginning treatment can be life-threatening, effective and rapid diagnosis is essential. Failure to diagnose and treat bacterial meningitis early can result in morbidity with serious, long-term complications including brain damage, hearing loss, learning disability, and death. When a patient presents symptoms of an infection, the physician may prescribe an antibiotic for a suspected bacterial infection before any testing has begun. There is an on-going clinical problem related to the fact that currently available methods cannot effectively culture bacteria in cerebrospinal fluid obtained from "pre-treated" patients, thus making it difficult to confirm the bacterial diagnosis using growth-detecting methods. Rapid and reliable detection of the pathogen and determination of the susceptibility of the pathogen to a particular pharmaceutical agent is of the utmost importance.

One method developed and used to detect the presence of viable cells faster is the impedance sensing of biological samples that measures metabolic deviations to monitor the proliferation of cells and subsequent population growth. Historically, impedance sensing has been used as an electronic analog of the Petri dish to monitor the proliferation of cells and subsequent population growth. Commercially available systems using this approach typically measure either conductance, capacitance, or the full impedance vector, that is, both resistive and reactive components, and use geometries with detection thresholds that require growth up to a million Colony Forming Units per milliliter ($10^6$ CFU/ml) or greater in the case of bacteria. However, obtaining that high titer requires significant time, especially if the bacteria belong to a slow-growing species.

Thus, a need exists for new, rapid, and improved methods of detecting viable cells and determining their susceptibility to an external agent or environmental factor. The present invention fulfills this need. Various embodiments of the disclosed invention provide such methods and diagnostic tools that yield test results significantly faster than conventional methods relying on growth or biomass increase.

SUMMARY OF THE INVENTION

The inventors of the disclosed subject matter have now discovered a method of monitoring a stress response from a cell, using impedance sensing to obtain this information. The change in impedance from a cell suspension caused by the stress response of living organisms to a stressor is immediate and more intense than the change in impedance from a cell suspension resulting from growth. The method described herein directly monitors changes in the level of stress response induced by different stressors by sensing changes in the impedance of a cell suspension. From these changes one can infer the presence or absence of viable cells, and the susceptibility of the cells to different stressors. The invention inter alia includes the following, alone or in combination.

In one embodiment, the invention relates to a method for rapidly monitoring a stress response of a cell to a stressor, and determining the magnitude of the stress response, the method comprising: a) under conditions suitable for monitoring the voltage and/or the current, applying an electric field to a test sample comprising the cell and a medium; b) monitoring the voltage and/or the current; c) allowing a stressor to impact the test sample, wherein the stressor is chosen from a stressor applied prior to, a stressor applied substantially simultaneously with, and a stressor applied subsequent to the applying of the electric field; d) monitoring an initial impedance response of the test sample, wherein the initial impedance response of the test sample is an impedance change of the test sample during the period of transition from a first measurement of impedance of the test sample at about the time of applying the electric field up to and including a subsequently measured impedance of the test sample that is indicative of the stress response or non-growth, thereby monitoring the stress response of said cell to the stressor; and e) determining the level of the initial impedance response of the test sample, wherein the level of the initial impedance response of the test sample is an indication of the magnitude of the stress response of the cell, thereby determining the magnitude of the stress response of the cell to the stressor.

The present invention relates, in another aspect, to a method for rapidly detecting the presence of a cell in a test sample, for example, the presence of pathogenic microorganisms in a sample of tissue fluid. For example, disclosed herein is a method for rapidly detecting the presence or absence of a cell by monitoring a stress response of the cell if said cell is present, or the absence of the stress response if said cell is absent or dead, the method comprising: a) under conditions suitable for monitoring the voltage and/or the current, applying an electric field to a test sample; b) monitoring the voltage and/or the current; c) allowing a stressor to impact the test sample, wherein the stressor is chosen from a stressor applied prior to, a stressor applied substantially simultaneously with, and a stressor applied subsequent to the applying of the electric field; d) at a specific time point or over a series of time points, measuring an initial impedance response of the test sample, wherein the initial impedance response of the test sample is an impedance change of the test sample during the period of transition from a first measurement of impedance of the test sample at about the time of applying the electric field up to and including a subsequently measured impedance of the test sample that is indicative of the stress response or non-growth, and e) assessing the level of the initial impedance response of the test sample at each time point, wherein the level of the initial impedance response of the test sample at each time point is an indication of the level of the stress response of said cell, thereby monitoring the stress response of said cell to the stressor if said cell is present in the test sample, or the absence of the stress response if said cell is absent from the test sample or dead; and thereby rapidly detecting the presence or absence of said cell in the test sample.

Yet another embodiment of the invention is a method for determining a predictive outcome for the susceptibility of a cell to a selected concentration of a bio-active agent and a level of stress of the cell at the selected concentration of the bio-active agent, wherein the level of susceptibility of the cell is previously known or unknown, the method comprising: a) i) at specific time points or over a series of time points, measuring an initial impedance response of a test sample comprising: the cell, a medium, and the selected concentration of the bio-active agent; and measuring an impedance response of a reference sample comprising the medium and the selected concentration of the bio-active agent, wherein said reference sample is devoid of cells; ii) determining a First Impedance Response Treated Profile at each of the time points, wherein the First Impedance Response Treated Profile is a mathematical comparison of the initial impedance response of the test sample determined in step a) (i) and the impedance response of the reference sample determined in step a) (i) at each time point; iii) optionally, repeating steps a) (i) and a) (ii) for a plurality of selected concentrations of the bio-active agent to obtain the corresponding First Impedance Response Treated Profile for each different selected concentration of the known bio-active agent; b) i) at the specific time points or over a series of time points, measuring the initial impedance response of a second test sample comprising the cell and the medium, wherein the second test sample is devoid of the bio-active agent; and measuring the impedance response of a reference sample comprising the medium, wherein said reference sample is devoid of cells; ii) calculating a First Impedance Response Untreated Profile, wherein the First Impedance Response Untreated Profile is a mathematical comparison of the initial impedance response of the second test sample determined in step b) i) and the impedance response of the reference sample determined in step b) i) at each time point; c) for each selected concentration of the bio-active agent, determining a Normalized Impedance Response value, NIR, wherein the NIR is a numerical value determined by an algorithm relating the First Impedance Response Treated Profile value obtained in step a) ii), and/or step a) iii), to the First Impedance Response Untreated Profile value obtained in step b) ii), such that the First Impedance Response Untreated Profile value is incorporated in the NIR, and wherein the determined NIR value is a quantitative measure of the level of stress of the cell at the selected concentration of the bio-active agent.

Also disclosed herein are kits comprising materials that are helpful or required for carrying out a method of the invention, and a set of instructions for use of the kit.

The methods and kits according to various embodiments of the invention facilitate the rapid and reliable detection of viable cells, identification of pathogens, and determination of the susceptibility of a pathogen to a particular drug.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
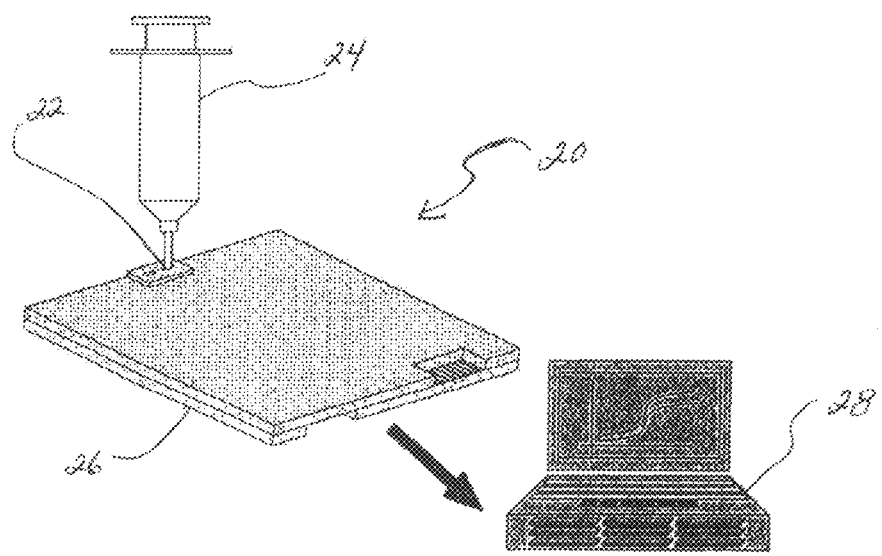
FIG. 1 is a schematic diagram for a cassette concept, showing a cassette based on a planar geometry.

A description of preferred embodiments of the invention follows. It will be understood that the particular embodiments of the invention are shown by way of illustration and not as limitations of the invention. At the outset, the invention is described in broad, overall aspects, with more detailed descriptions of some aspects following. The features and other details of the compositions and methods of the invention will be further pointed out in the claims.

The present invention is directed to methods and diagnostic kits for rapidly detecting the presence of viable cells, identifying the cell type, and rapidly determining the susceptibility of the cell to an external agent. The invention provides significantly faster detection of viable cells and their corresponding susceptibilities compared to currently-used methods which rely on detecting biomass increase due to the growth-of cultured cells or the lack thereof.

In broad terms, one aspect of the invention provides a method for monitoring a stress response from a cell to a stressor, using impedance sensing to obtain this information.

In another aspect, the invention relates to detecting the presence or absence of a viable cell, using impedance sensing to monitor the stress response of the cell to a stressor.

In yet another aspect, the invention provides a method for determining the susceptibility of a cell to a selected concentration of a stressor comprising a bio-active agent, and a level of stress of the cell at the selected concentration of the bio-active agent, using impedance sensing to achieve this determination.

The Stress Response

The growth of a viable cell population is determined by the multiplication of one or more cells comprising that population. During that growth, cells utilize available nutrients in order to accumulate energy predominantly in the form of ATP as well as NADPH and phosphoenolpyruvate (PEP), and synthesize biological macromolecules, such as DNA, RNA, proteins, lipids, and carbohydrates. For example, in the case of bacteria, all of these components are subsequently used to produce two new daughter cells by the process known as binary fission. If culture conditions remain favorable, both new cells will repeat this cycle. This usually occurs during growth, also called logarithmic growth.

However, if cells experience unfavorable conditions, such as a hostile environment, they respond with a dramatic metabolic deviation, halting growth processes, and entering into a survival mode known as the "stress response". Consequently, regular protein synthesis is rapidly suppressed, while new regulons are activated resulting in an enhanced tolerance of the cells for the stress factor, also referred to herein as the "stressor".

Stressors can comprise chemical stressors, physical stressors, and biological stressors. Non-limiting examples of chemical stressors include detergent treatment, alcohol treatment, antibiotic treatment, acidification or alkalization, oxidation, and contact with heavy metals. Non-limiting examples of physical stressors include temperature shift, acoustic waves, pressure shock, osmotic pressure change, ionizing radiation, electric shock, and electromagnetic radiation. Non-limiting examples of biological stressors include changes in media conditions, stationary phase after growth, nutrient deprivation, including, for example, carbon or nitrogen starvation, and hypoxia. As used herein, the terms "stress" and "stressor" refer to any combination of stressors which may be applied, modified and/or removed at various times. Under certain conditions of applied voltage and/or current, the measurement of impedance itself may be considered a stressor and can be used either alone or in conjunction with other stress factors. Activation of the stress response machinery usually occurs within minutes after the appropriate stimulus is applied and peaks at about 10 to 30 minutes, depending on the species. This response may last up to several hours or more depending on the severity of the stress. This period, which may be a different actual length for exceptional cell types, will be referred to as the initial response period.

The chemical stressors, physical stressors, and biological stressors are bio-active agents. As the term is used herein, "bio-active agent" has the same meaning as "biologically active agent" and refers to any agent or substance that has or is capable of demonstrating any in vivo or in vitro activity. Non-limiting examples of chemical and biological bio-active agents useful in an embodiment of the invention include therapeutic substances and pharmaceutical agents, such as antimicrobial agents, antibiotics, thrombin inhibitors, antithrombogenic agents, thrombolytic agents, fibrinolytic agents, vasospasm inhibitors, calcium channel blockers, vasodilators, antihypertensive agents, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives (including antiangiogenesis agents), anticancer chemotherapeutic agents, anti-inflammatory steroid or non-steroidal anti-inflammatory agents, immunosuppressive agents, hormones, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents.

According to an embodiment of the invention, a stressor, such as a bio-active agent is applied to the cell by a method comprising contacting the cell with the bio-active agent. In a particular embodiment, the bio-active agent is chosen from a pharmaceutically active agent, such as an anti-cancer agent; a biological toxin; a virus; and another substance capable of producing stress, and combinations thereof.

The stressor can create a stress or biotic stress or physiological stress. As used herein, the terms "stress" and "biotic stress" have the same meaning and refer to any adverse effect on metabolism, growth or viability of a cell population. The adverse effect can be produced by a living organism, a non-living or non-biological environmental stressor, such as temperature change.

The stress response is characterized by significant retardation and/or redirection of most of the metabolic processes related to growth. These include a decrease in the level of ATP, NADPH, and PEP; inhibition of replication, and the increase of condensation of DNA, together with local denaturation in super-coiled DNA. In addition, RNA transcription, protein translation, and lipid and carbohydrates synthesis are also down-regulated.

At this stage, stressed cells enter conditions which are characterized as cell division arrest. Consequently, all cells become synchronized in the same stage of their "growth cycle" and hence the majority of cells will begin cell division at a similar time after successfully transitioning through the stress period. As an example, for fast-growing bacteria, *Pseudomonas putida*, cell division arrest after stress can last as long as four hours.

Overall, the genes encoding stress response proteins are highly conserved among various species. Although some details of the stress responses to different factors, such as, for example, heat-shock, SOS, and oxidative stress, may differ at the molecular level, in most cases heat shock proteins (hsp) play the most important role in cell survival during and after the initial stress. Stress response proteins, especially hsp, are described for virtually all single-celled organisms and multicellular organisms of both prokaryotic, including the smallest known self-replicating cell, *Mycoplasma genitalium*, and another obligate intracellular bacterium, *Chlamydophila trachomatis*, and eukaryotic origin, including algae, plants, fungi, protozoa, animal and human cells. Even eukaryotic cell organelles, such as mitochondria and chloroplasts, encode their own hsp.

Deviations in cellular metabolism are manifested by changes in the dielectric properties of a cell suspension. Cellular metabolism modifies the dielectric, reflecting a net change of charged compounds from metabolic products, changes in cell morphology, surface charge effects, and synthesis of highly charged molecules, such as DNA and RNA, along with salts, proteins, amino acids and other constituents that may be present in the medium. In an embodiment, these changes to the dielectric properties of a cell suspension are measured by recording changes in the electrical impedance of the corresponding suspension.

We have now discovered that the change in impedance value in a cell suspension caused by the stress response of living organisms to a stressor is immediate and more intense than the change in impedance value in a cell suspension resulting from growth. The method described herein directly monitors changes in the stress response of cells induced by different stressors by sensing changes in the impedance of a cell suspension. From these changes one can infer the presence or absence of viable cells, and the susceptibility of the cells to different stressors.

Although the impedance response from a suspension of cells is known to result from metabolic activities of the cells, the full capabilities of impedance sensing have been underutilized to date. Some prior works may have used the broader term metabolic deviations (also referred to as metabolic activity) to refer to growth, but as used here, the term "metabolic deviations" is intended to refer to all of the biological processes within the cell, not only those that are directed toward growth and reproduction. We disclose the measurement of impedance to detect the metabolic deviations associated with the stress response, rather than just those associated with growth. We have demonstrated the utility of these capabilities of impedance sensing to indicate the presence of different species of bacteria by monitoring the initial metabolic deviations of stressed cells.

The Cells

It is important to note that the stress response is general and not unique to any one cell or microorganism. Thus, the disclosed approaches are applicable to all prokaryotic cells or eukaryotic cells. The disclosed methods are particularly useful for determining the presence or absence of a pathogen and the susceptibility of the pathogen to a given concentration of a bio-active agent, such as an anti-microbial agent.

The methods according to various embodiments of the invention include, for example, a method for rapidly monitoring a stress response of a cell to a stressor and determining the magnitude of the stress response; a method for rapidly detecting the presence or absence of a cell by monitoring a stress response of the cell if said cell is present, or the absence of the stress response if said cell is absent or dead; and a method for determining a predictive outcome for the susceptibility of a cell to a selected concentration of a bio-active agent and a level of stress of the cell at the selected concentration of the bio-active agent, wherein the level of susceptibility of the cell is previously known or unknown. The disclosed methods are particularly of use for testing bacteria, including pathogens of non-bacterial origin.

As used herein, the term "detecting" is intended to include, although is not limited to, determining the presence or absence of a cell, or quantifying the amount of the cells. The term thus refers to the use of the materials, compositions, and methods of the present invention for qualitative and quantitative determinations Examples of eukaryotic cells suitable for use in a method according to an embodiment of the invention include protists, protozoa, fungi, a non-transformed human cell, a non-transformed animal cell, a transformed human cell, and a transformed animal cell, with the proviso that if the eukaryotic cell is adhesion-dependent, the test sample medium additionally comprises suspended micro culture beads comprising a coating of an extracellular matrix capable of adhesion with the eukaryotic cell.

It may be necessary or useful for a particular type of prokaryotic or eukaryotic cell, that the test sample medium and the reference sample medium additionally comprise suspended beads comprising a coating of specific receptors capable of adhesion with the prokaryotic or eukaryotic cells. The receptors can comprise biologically active components chosen from: components generated from immunological responses, components generated from nucleic acids, and components generated from other chemical or biochemical compounds that can be used to identify specific cells.

The Media And the Sample

A media suitable for use in a method according to an embodiment of the invention can be chosen from: one which will not support the viability of the cell and one which will support the viability of the cell for a period of time sufficient to measure a stress response. The choice of media will depend on the cell type and the nature of the test to be performed. Non-limiting examples of suitable media include commercially available culture media, aqueous broths, gels, and agar-based media. In a preferred embodiment the media have some electrically conductivity.

As used herein, "sample" refers to anything which may contain a moiety to be isolated, manipulated, measured, quantified, detected or analyzed using suitable devices according to the disclosed methods. The sample may be a biological sample, such as a biological fluid or a biological tissue or an environmental or industrial sample containing biological or suspected biological material. Examples of biological fluids include suspension of cells in a medium, such as cell culture medium, urine, blood, plasma, serum, saliva, semen, stool, sputum, cerebral spinal fluid, tears, mucus, amniotic fluid or the like.

Examples of environmental or industrial samples include suspensions of cells in a water sample, a cosmetic sample, a food sample, a pharmaceutical sample, or the like.

Measuring Initial Impedance Response

The use of electrical impedance measurements to monitor cell growth is well-established. Commercially available systems using this approach typically measure conductance, capacitance, or the full impedance (both resistive and reactive components) and use geometries that require significant growth in order to be detected. In the case of bacteria, the typical growth threshold needed for detection with these systems is one million ($10^6$) CFU/ml or greater. Obtaining that high titer requires significant time, especially if the bacteria belong to slow-growing species.

Embodiments of the present invention use impedance sensing in a way that allows for significantly more rapid detection of viable cells by detecting the impedance change due to stress response. The impedance response from a cell suspension correlates with the integrated metabolic activities within that suspension and provides significantly more information than other non-invasive methods that detect only increases in biomass during cell multiplication and the corresponding population growth. Moreover, metabolic deviations can occur without cell division, and such metabolic changes would thus not be detected by other systems that rely on increases in biomass due to cell multiplication and the corresponding population growth. Thus, the disclosed methods of impedance sensing and analysis provide improved detection and analysis of cell stress in cell suspensions.

In general, the term "impedance" can be used to describe the bulk electrical properties of a sample and its respective ability to impede the flow of current. Impedance can be measured with time varying potentials or currents at some specified frequency. If a sinusoidal AC voltage is applied across the sample volume, at some frequency, v, a current will flow through the medium. The current, while alternating at the same frequency as the voltage will have some phase relationship to the applied voltage. The impedance of the sample is defined by the ratio of the magnitudes of the voltage and current and the relative phase angle between them.

The physical interpretation of the impedance measurement is best described by the following two components: the resistive component and the reactive component. Resistance and reactance are properties which must be combined to find the impedance of a system. However, terms, such as "resistance" and "reactance" are sometimes loosely referred to as "impedance", or as a representation of impedance.

Alternatively, any known time-varying signal containing a set of frequency components can be used to drive a sample for the purpose of determining impedance parameters associated with the sample. In general, this signal can be a voltage, a current, or some combination of voltage and current. It can contain many different frequency components simultaneously, and in the case of "bandlimited white noise", it can contain every frequency within a certain bandwidth. Using any of these drives, a corresponding response of current, voltage, or voltage and current can be measured. At any given frequency, the impedance of the sample is the ratio of complex voltage to complex current. This impedance can be represented by a pair of numbers, such as magnitude and phase, or real and imaginary. Under certain conditions, the response may contain frequency components that were not in the drive signal and therefore may contain additional information about the sample.

Alternating current (AC) allows for easier determination of a critical property, the capacitance that is relevant to the methods according to various embodiments of the present invention. A simple capacitor may comprise a pair of electrical conductors, such as metal plates, separated by a non-conductor or insulator. The amount of separated electrical charge that can be stored or held on the capacitor per unit of electrical potential between the conductors may be referred to as its capacitance. Measurements of a cell suspension encompassed by two electrodes can be thought of as a biological capacitor.

Although the examples presented here use measurements of capacitance to monitor a stress response, it is also within the scope of this disclosure to use any other appropriate one-dimensional or multi-dimensional electrical measurements, such as conductance, susceptance, admittance or any other representation(s) or transformation(s) of the impedance vector to measure the stress response of cells without departing from the scope of the invention encompassed by the appended claims. With no more than routine experimentation or simple adjustments, those skilled in the art could utilize not only capacitance to measure the stress response according to an embodiment of the invention, but also all representations of electrical measurements, such as impedance. Furthermore, applying an electric field may be accomplished by a variety of means including any combination of voltage and/or current. Any and all references to a dielectric may include its complete, "non-ideal" characterization and not be restricted to its reactive component of impedance.

Although the differing times between growth and stress responses provide much valuable information, there is also an enormous amount of information contained in the impedance response. Even for a relatively simple set of impedance measurements, each individual impedance value measured over a sample interval is no less than a two-dimensional vector and the change between every pair of samples is at least a two-dimensional vector. Thus, even for a simple drive signal, a large number of change vectors and their derivatives can result. In addition to this substantial amount of information about the nature of the cellular response, a separate set of vector data points can be generated for every possible drive signal. Each drive signal may be composed of a single frequency component or any realizable set of frequencies. Furthermore, the system can switch between various different drive signals during the testing of a single sample to generate even more information. Under certain circumstances, the output frequencies will be different than the input frequencies, thus providing even more information within the impedance response profile. It can be difficult for one to think about or visualize the enormous amount of information that is contained within the impedance response, and therefore, simpler representations are often used. For example, references to capacitance, resistance, reactance or positive and negative signals can be convenient for representing and interpreting the results. This vast multidimensional space of the impedance response can be mathematically transformed into an infinite number of one-dimensional or multi-dimensional representation spaces. Of course, it is possible to align or transform a coordinate space to have its axes better correspond to any particular behavior or property of interest.

Thus, for example, any reference to a particular sign or quantity could easily be changed mathematically without impacting the principles underlying this invention. In one embodiment of the invention, differential methods are used in order to obtain an improved level of precision. In one embodiment, resulting impedance profiles reflect a comparison of measurements from a pair of sterile, mechanically identical chambers. For example, the first chamber can be filled with a medium containing stressed cells, while the second chamber contains sterile medium and no cells. Alternatively, the first chamber can be filled with medium and un-stressed cells, and a stressor can be added to the medium. The second chamber, serving as a reference, is positioned in close proximity to the first, so that both volumes are subjected to nearly identical thermal and mechanical perturbations, providing a means for common-mode rejection. A small alternating current (A.C.) voltage is applied across the two electrodes, creating a parallel plate capacitor.

Stressed cells in the first chamber change the dielectric properties of the cell suspension in response to the stress. Some changes in the dielectric can also be seen in the second chamber derived from interactions between organic compounds in the medium, also common to the first chamber. The changes in the impedance profiles of the samples in both chambers over time are compared. Any differences detected between the two samples reflect the cellular activities caused exclusively by the stress response of the organisms.

According to an embodiment of the invention, at a specific time point or over a series of time points, an initial impedance response of a test sample of the cell suspension following application of a stressor is measured. As the term is used herein, the "initial impedance response" of a sample, such as the test sample, is an impedance change of the test sample during the period of transition from a first measurement of impedance of the test sample at about the time of applying the electric field up to and including a subsequently measured impedance of the test sample that is indicative of the stress response or non-growth. In one embodiment of the invention, the subsequently measured impedance of the test sample can be at time when the non-growth would begin to be detected.

The "initial impedance response" as described above can refer to a period of transition of a measurement of impedance of the test sample. Alternatively, the "initial impedance response" can refer to a period of transition of a measurement of impedance of a sample modified by a related measurement obtained at about a similar time.

Further, according to another embodiment of the invention an Impedance Response Profile (IRP) of the test sample is determined. The IRP is based on the mathematical comparison of the level of the measured initial impedance response of the test sample with a standard value. Alternatively, the IRP can be based on a mathematical comparison of a measurement of the impedance of a test sample with a standard value prior to the mathematical construction of the initial impedance response. The standard value can be the measured initial impedance response value or the measured impedance of a first reference sample comprising the medium with or without the stressor, and wherein the first reference sample is devoid of cells. Alternatively, the standard value can be the measured initial impedance response value or the measured impedance of a second reference sample comprising the cell and the medium, wherein the cell is of the same concentration as the cell in the test sample, wherein the second reference sample is devoid of the stressor, and wherein the initial impedance response of the second reference sample is an impedance change of the second reference sample during the period of transition from a first measurement of impedance of the second reference sample at about the time of applying an electric field up to and including a subsequently measured impedance of the test sample that is indicative of the stress response or non-growth.

The IRP reflects the metabolic deviations occurring within the suspension of cells. In one embodiment, when the value of IRP is constantly increasing over a period of time significantly exceeding the doubling time of the cell population, growth is occurring. When the value of the IRP is decreasing over a period of time less than or approximately equal to the doubling time of the cell, stress is occurring. Hence, the absence of growth (i.e. cell division) for cells under stress is defined by the measurement of a second value of the IRP that is lower than the value recorded in a first earlier measurement by an amount exceeding the statistical uncertainty of the two measurements. While a decrease of the value of the IRP is sufficient to determine stress, it is not always necessary. In some cases, the assessment of stress or the absence of growth can be recognized by both statistically significant increasing values of the IRP followed by subsequent decreasing values, or statistically significant decreasing values of the IRP followed by subsequent increasing values over a period of time less than or approximately equal to the doubling time of the cell population. Stress can also be inferred by an IRP from stressed cells that is less than the IRP from cells that are un-stressed.

The end of the period of stress and the corresponding start of growth can be determined by the impedance response profile at a time greater than the doubling time of the cell population at a point of infection where the slope of the impedance response profile changes from a negative slope to a positive slope.

The measurement of the stress response can also be differentiated from growth by comparing the response profiles to data sets from previously recorded experiments. By matching the impedance behavior to known responses from similar experiments, a determination can be made at a specific time for any desired statistical confidence interval. As greater statistical confidence is desired, the length of time comprising the initial impedance response can be extended. Also, the degree to which the results. being measured match stored sets of expected values may also extend the initial impedance response in order to increase statistical confidence. In the following examples, the stress and growth responses are distinct and their parameterization may be adjusted by using the doubling times of the particular cell populations within the sample being tested.

Following determination of the IRP, analysis of the IRP can enable, for example, detection of a cell, determination of information regarding the response of a cell to a given stressor, and determination of the susceptibility of a cell to a given concentration of a bio-active agent.

Turning now to the drawings, as depicted schematically in FIG. 1, an embodiment of the disclosed impedance technology can be implemented in an easy-to-operate, relatively low-cost device. For example, the system can be designed using a cassette housing a panel of sensitive test chambers. The cassette may be of a disposable type. In one embodiment of the invention, all sensing elements are integrated within a planar mesoscale sized cassette having a form factor similar to a credit card and ideal for established mass production techniques. The use of mesoscale geometry enables the testing of samples with practical volume sizes without the additional concentration of cells while generating signals having high signal gain for sensitive measurements. Once filled with, for example, media, and treated or untreated test samples, the cassette can be inserted into a readout fixture that monitors the impedances, analyzes, displays, and records the information. An example of a conceptual design of a multiple cassette device, a notebook-sized impedance biosensor, for use in an embodiment of the invention is shown in FIG. 1.

Figure 2:
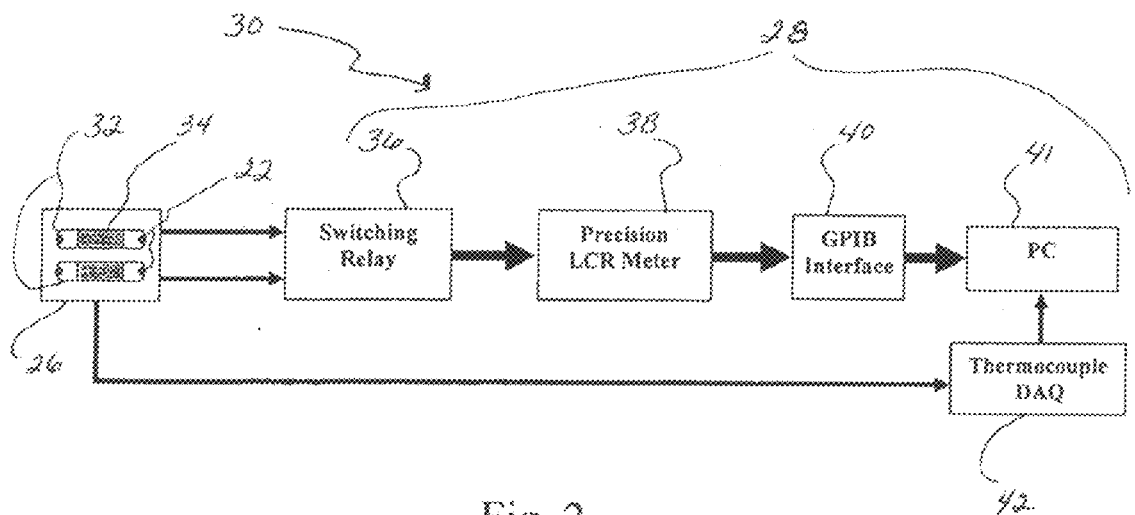
FIG. 2 is a schematic diagram depicting an impedance monitoring detection system.

FIG. 1 is a schematic diagram for a cassette (20), showing a cassette (26) based on a planar geometry. Internal to each cassette (26) is a panel of detection chambers (32) as shown in FIG. 2. Each chamber (32) is constructed with two electrodes (34) having relatively small separation gaps. As used herein, the term "electrode" is a structure having a high electrical conductivity, that is, an electrical conductivity much higher than the electrical conductivity of the surrounding materials. A test sample is injected by the user directly into a fill port (22) located on the cassette (26) and the sample is distributed to the detection chamber (32). The cassette (26) is inserted within an analyzer device (28) for readout. The electrical impedance of each chamber is recorded, monitoring the respective changes in the dielectric properties of the cell suspensions.

Although two electrodes (34) are used in these examples, the invention may be embodied in a system that uses more than two electrodes (34) per chamber (32). Each electrode (34) may be composed of one or more materials that may or may not produce an electrochemical effect within the sample.

Stress may be applied to the test samples by allowing a stressor to impact the test sample, wherein the stressor is chosen from a stressor applied prior to, a stressor applied substantially simultaneously with, and a stressor applied subsequent to the applying of the electric field or the filling of the detection chambers (32).

FIG. 2 is a schematic block diagram (30) depicting an impedance monitoring detection system. The platform comprises a cassette (26) containing multiple detection chambers (32), each chamber (32) having two electrodes (34); and an analyzer (28), as shown schematically in FIG. 1, that accepts the cassette (26), and monitors the stress response of a cell suspension in real-time. The analyzer (28) comprises the switching relay (36), the Precision LCR meter (38), the GPIB Interface (40), the computer or PC (41), and the Thermocouple DAQ (42).

A generalized description of operation of the system according to an embodiment of the invention follows. A manually filled meso-scale research grade test cassette (26) with two independent biological samples in separate detection chambers (32) is inserted into a thermally insulated mounting fixture to hold the cassette (26) stable during measurement, maintain thermal stability, and make electrical contact with the analyzer (28). The fixture includes two thermally controlled platens on which electrical guards are mounted to shield the cassette (26) from stray capacitances. The temperature of the platens is monitored using an embedded thermocouple, and recorded using a data acquisition system (DAQ) (42) (such as those manufactured by National Instruments). The impedance may be measured using a commercially available meter, AGILENT® 4284A Precision LCR meter (38) (AGILENT® Technologies, Inc., Palo Alto Calif.). This impedance meter (38) was capable of monitoring only a single channel at any one time and therefore a switching relay box (36) was built to toggle between the two detection chambers (32). The AGILENT® meter (38) communicated with a computer (41) using a standard GPIB board interface (40). The computer (41) recorded, analyzed, and displayed the data. A software program (available from BioSense Technologies, Inc., Woburn, Mass.), was written to provide an easy-to-use interface for both running experiments and performing basic analysis.

In the example illustrated, the system operated on alternating current (A.C.) with measurements made at about one kiloHertz (1 kHz); however adjustments can be made with no more than routine experimentation.

The impedances of the two detection chambers (32) are recorded monitoring changes in the dielectric properties of the biological suspension. As described above, the respective dielectric properties are modified due to cellular metabolism by the net change of charged compounds from metabolic products, changes in cell morphology, surface charge effects, DNA, RNA, and other highly charged molecules, such as proteins and amino acids.

The comparison used to determine the IRP for Example 1 was the ratio of the capacitive component of the impedance at each measurement time of the chamber containing cells to that with medium only.

A disclosed method for rapidly monitoring a stress response of a cell to a stressor, and determining the magnitude of the stress response, comprises: a) under conditions suitable for monitoring the voltage and/or the current, applying an electric field to a test sample comprising the cell and a medium; b) monitoring the voltage and/or the current; c) allowing a stressor to impact the test sample, wherein the stressor is chosen from a stressor applied prior to, a stressor applied substantially simultaneously with, and a stressor applied subsequent to the applying of the electric field; d) monitoring an initial impedance response of the test sample, wherein the initial impedance response of the test sample is an impedance change of the test sample during the period of transition from a first measurement of impedance of the test sample at about the time of applying the electric field up to and including a subsequently measured impedance of the test sample that is indicative of the stress response or non-growth, thereby monitoring the stress response of said cell to the stressor; and e) determining the level of the initial impedance response of the test sample, wherein the level of the initial impedance response of the test sample is an indication of the magnitude of the stress response of the cell, thereby determining the magnitude of the stress response of the cell to the stressor.

The disclosed method for monitoring a stress response of a cell and determining the magnitude thereof, can further comprise mathematically comparing the level of the initial impedance response of the test sample determined in step (e) with: (i) a first standard value that represents the impedance response of a first reference sample comprising the medium with or without the stressor, and wherein the first reference sample is devoid of cells; and/or (ii) a second standard value that represents the initial impedance response of a second reference sample comprising a cell and the medium, wherein the cell in the reference sample is of the same type and concentration as the cell in the test sample, and wherein the reference sample is devoid of the stressor; and determining a value for a First Impedance Response Profile of the test sample, the value for the First Impedance Response Profile based on the mathematical comparison of the level of the initial impedance response of the test sample determined in step (e) with the first standard value and/or the second standard value.

Example 1 relates to an experiment demonstrating an immediate initial impedance response from heat-shock stressed *E. coli* as compared to un-stressed *E. coli*.

EXAMPLE 1

Initial Impedance Response From Heat-Shock Stressed Bacteria

It is known that bacterial metabolism following heat shock deviates significantly from that of unshocked bacterial cells. In this example, the ability to measure the initial impedance response from stressed bacterial cells during this recovery period is shown. First, the initial impedance response from un-shocked *E. coli* was measured. A single colony from overnight culture on Luria-Bertani Agar (LBA) (Becton Dickinson Microbiology Systems, Sparks, Md.) was picked with a sterile loop, re-suspended in TSB, and after appropriate dilution to approximately 1,000 Colony Forming Units per milliliter ($10^3$ CFU/ml) transferred directly into one of the impedance cassette chambers while the adjacent chamber was filled with TSB only. The cassette was inserted into the thermally controlled analyzer held at 37 degrees Celsius (37° C.) and the full impedance vector was recorded. In the data presented here, the capacitance components of the initial impedance signals were analyzed. A similar effect can be seen by analyzing other representations of the impedance vector.

To measure the response of stressed bacteria, a single colony from overnight culture on LBA was picked with sterile loop, re-suspended in phosphate buffered saline (PBS) and heated at 45 degrees Celsius (45° C.) for 30 minutes. After the shock treatment was applied, the bacterial suspension was diluted in TSB and transferred directly into one of the cassette chambers while the adjacent chamber was filled with TSB. As before, the cassette was inserted into the thermally controlled analyzer held at 37 degrees Celsius (37° C.) and the capacitance signals were recorded.

Figure 3:
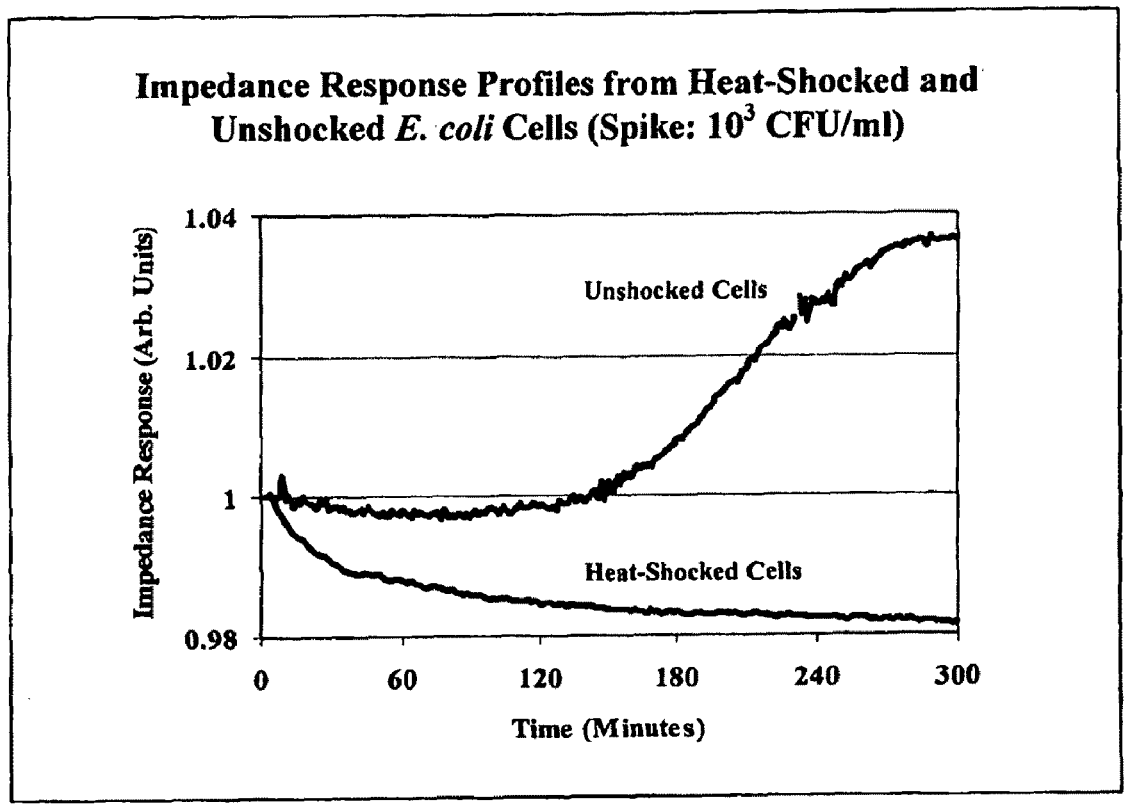
FIG. 3 is a graph representing the impedance response from un-shocked (top curve) *Escherichia coli* (*E. coli*), and the initial impedance response from heat-shocked (bottom curve) *E. coli* in tryptic soy broth (TSB) medium at 37° C.

The "Impedance Response Profile", here represented as the ratio of the respective capacitances of the chamber containing shocked cells to that with TSB only, is presented in FIG. 3. FIG. 3 is a graphical representation of the Initial Impedance Response Profile for the un-stressed (top curve) and the heat-shocked (bottom curve) *E. coli* in TSB at 37 degrees Celsius (37° C.). Initial titers were $5.6\times10^3$ CFU/ml for the un-stressed cells and $4.4\times10^3$ CFU/ml for the heat-stressed cells. As expected, after a typical lag phase delay of approximately 1.5 to 2.0 hours, the un-stressed bacteria started to grow and the corresponding value of the impedance response started to increase. In contrast, the impedance response from heat-shocked bacteria reveals the opposite trend, specifically, an immediate and constant decrease in the value of the impedance response was observed that continued throughout 5 hours of data taking. This decrease in the value of the impedance response is caused by the cellular stress response. Hence, the absence of growth (i.e. cell division) for cells under stress can be defined by the measurement of a second impedance response value that is lower than the value recorded in a first earlier measurement by an amount exceeding the statistical uncertainty of the two measurements. In this example, an unambiguous initial impedance response is recognizable with high statistical confidence in less than 30 minutes. This elapsed time is also within the approximate population doubling time for this bacterial species in the sample being tested. Taking into account that these cells are in cell division arrest caused by stress, this serves as evidence of the absence of growth during the time necessary for our measurements.

Thus, the impedance response from stressed viable cells and their consequent detection is both a faster and potentially more powerful than the impedance response observed during conventional growth (that is, cell proliferation).

To ensure that this decline was not due to bacterial death, bacterial enumeration was done by drop-plating and no significant differences in numbers of viable cells in the un-stressed and heat-shocked samples were found, further evidence that no cell growth or cell death occurred during the measurement time.

Detecting the Presence Or the Absence of A Cell

The disclosed method for rapidly detecting the presence or absence of a cell by monitoring a stress response of the cell if said cell is present, or the absence of the stress response if said cell is absent or dead, comprises: a) under conditions suitable for monitoring the voltage and/or the current, applying an electric field to a test sample comprising the cell and a medium; b) monitoring the voltage and/or the current; c) allowing a stressor to impact the test sample, wherein the stressor is chosen from a stressor applied prior to, a stressor applied substantially simultaneously with, and a stressor applied subsequent to the applying of the electric field; d) at a specific time point or over a series of time points, measuring an initial impedance response of the test sample, wherein the initial impedance response of the test sample is an impedance change of the test sample during the period of transition from a first measurement of impedance of the test sample at about the time of applying the electric field up to and including a subsequently measured impedance of the test sample that is indicative of the stress response or non-growth; and e) assessing the level of the initial impedance response of the test sample at each time point, wherein the level of the initial impedance response of the test sample at each time point is an indication of the level of the stress response of said cell, thereby monitoring the stress response of said cell to the stressor if said cell is present in the test sample, or the absence of the stress response if said cell is absent from the test sample or dead; and thereby rapidly detecting the presence or absence of said cell in the test sample. This method can be refined as described below.

The detection method can further comprise confirming the presence or absence of said cell in the test sample by: (i) measuring an impedance response of a first reference sample comprising the medium with or without the stressor, and wherein the first reference sample is devoid of cells; and/or (ii) measuring an initial impedance response of a second reference sample comprising said cell and the medium, wherein said cell is of the same concentration as said cell in the test sample, wherein the second reference sample is devoid of the stressor, and wherein the initial impedance response of the second reference sample is an impedance change of the second reference sample during the period of transition from a first measurement of impedance of the second reference sample at about the time of applying an electric field up to and including a subsequently measured impedance of the test sample that is indicative of the stress response or non-growth; comparing the initial impedance response of the test sample obtained in step (d) with the impedance response of the first reference sample and/or the initial impedance response of the second reference sample; and assessing the comparison of step (iii), thereby confirming the presence or absence of said cell in the test sample. Non-limiting examples of this method of detection include the following.

EXAMPLE 2

Specific Detection of Cells.

Figures 4A, 4B, 4C, 4D:
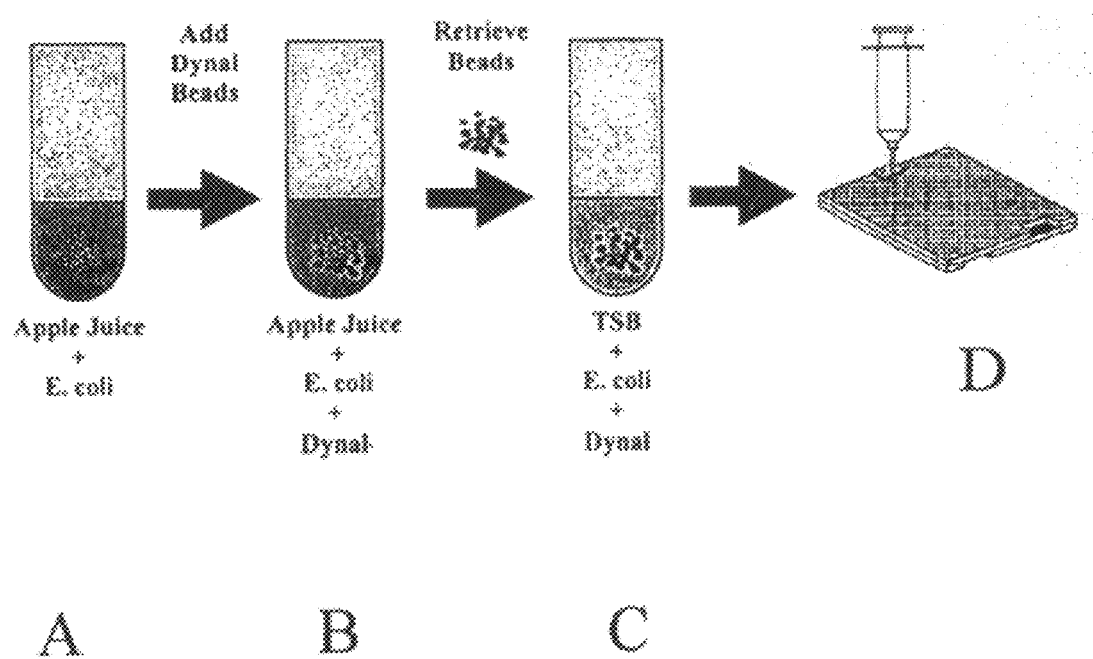
FIG. 4 is a schematic description of the experimental procedure according to an embodiment of the invention.

As a demonstration of the rapid and specific detection of cells in a sample, data are presented for the capture and detection of E. coli in apple juice. A series of experiments were conducted to compare the detection of E. coli in deliberately contaminated apple juice monitoring directly the growth and stress response. A schematic description of the experimental procedure is shown in FIG. 4. A 10 ml volume of sterile apple juice was spiked with approximately $10^3$ CFU/ml of E. coli O157:H7 (See FIG. 4A). Magnetic beads (Dynal Biotech, Oslo, Norway) pre-coated with antibodies specific for our strain on E. coli were added (See FIG. 4B).

Our protocol for cell capture strictly adhered to the manufacturer's recommendations. Once captured, the cell-antibody complexes were retrieved using the magnetic beads, and were washed and re-suspended in TSB (See FIG. 4C), and the resulting suspension was loaded into the cassette (See FIG. 4D). The adjacent chamber (reference) was loaded with similar medium but without cells. To study the stress response, bacteria recovered from the spiked apple juice were heat-treated for 30 minutes at 45° C. The impedance signals from these suspensions were recorded over time and analyzed. All suspensions were also enumerated using standard plating methods.

Results. The Impedance Response over a 14-hour period is plotted in FIG. 5 from the captured heat-shocked E. coli, along with measurements of similarly captured but un-stressed E. coli. The impedance response value from un-stressed cells (top curve) begins to increase at approximately 60 minutes and is unambiguously recognizable by 180 minutes (see FIG. 7). The curve eventually peaks at about 7 hours, followed by a decrease for about 2 hours before increasing once again. This increasing signal, peaking, and subsequent decrease has been correlated with oxygen consumption (hypoxic stress) and its eventual depletion in the growth medium, and corresponds to aerobic growth followed by hypoxia and anaerobic growth for the facultative anaerobe.

Figure 5:
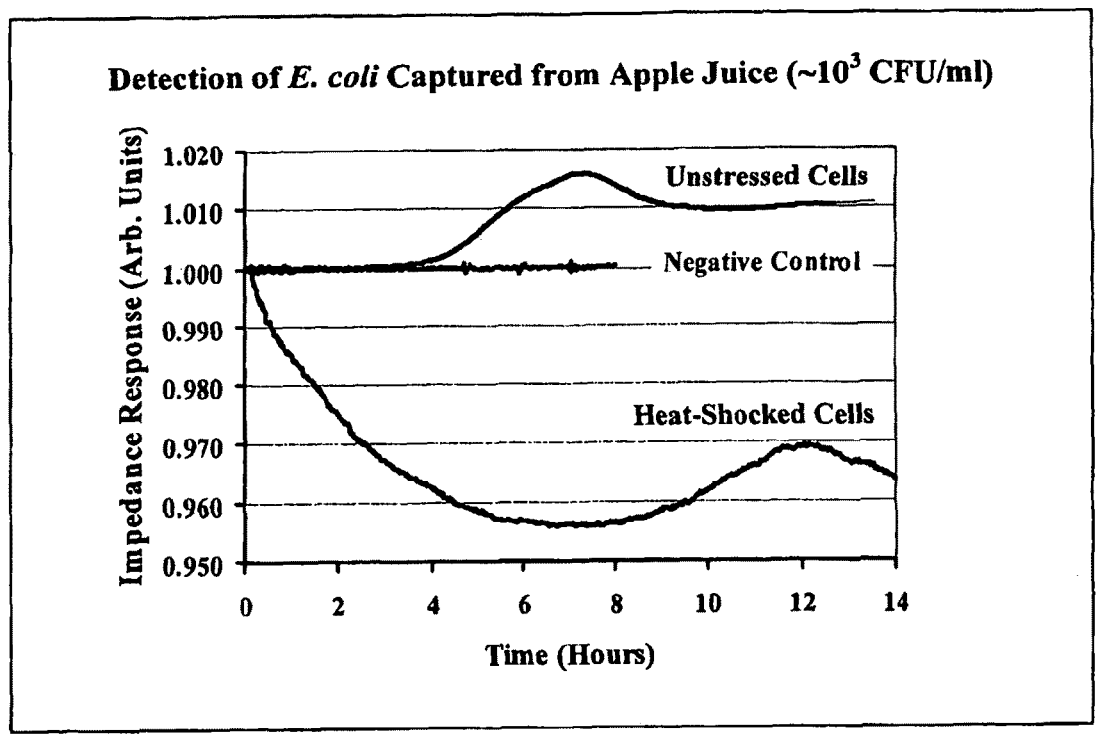
FIG. 5 is a graphical representation comparing the impedance response over a 14 hour period from stressed, that is, heat-shocked and from un-stressed *E. coli* captured from apple juice.

In FIG. 5 the impedance response from un-stressed cells is compared directly with the impedance response from stressed heat-shocked cells (lowest curve) having commensurate cell densities (approximately 1000 CFU/ml) along with a negative control containing no cells (flat, middle curve). The value of the impedance response during the cellular stress response is seen to dominate that from un-stressed cells both in intensity and detection time.

To further contrast the difference between stressed and un-stressed cell response, the value of the impedance response from the stressed cells immediately decreases reaching a minimum at 7 hours before exhibiting a response similar to that of normal or un-stressed cells. As is seen here, the recovery and subsequent re-entering into the growth state of the heat-shocked cells, as measured by their corresponding impedance response, is delayed by over 5 hours as expected. In addition, the intensity of the response is much greater and its onset is much faster than the impedance response from un-stressed cells, thereby demonstrating that the initial impedance response from the shocked cells is both stronger and more immediate than the impedance response for un-stressed cells.

Figures 6, 7:
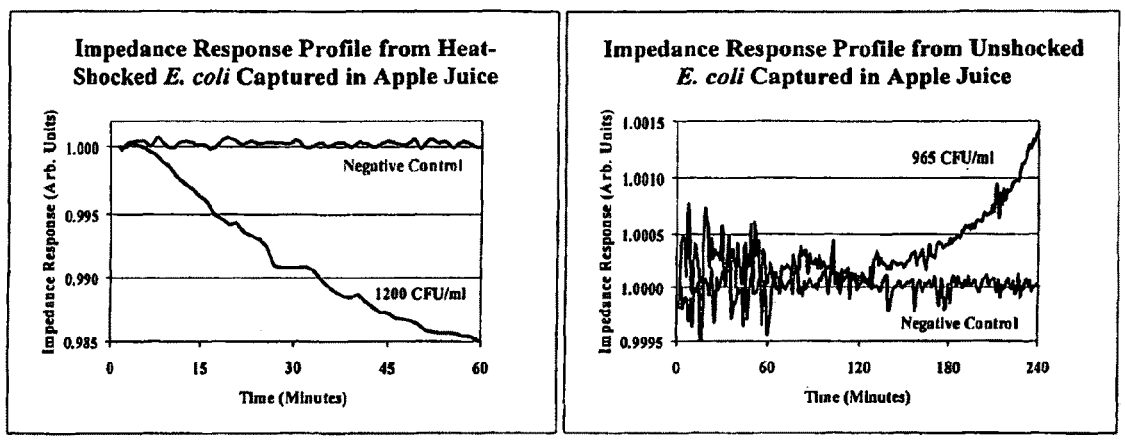
FIG. 6 is a graph representing the initial impedance response from heat-shocked *E. coli*.
FIG. 7 is a graph representing the impedance response from un-stressed *E. coli*.

The impedance responses during the initial measurement periods from the respective growth curves are plotted in FIG. 6 and FIG. 7 for side-by-side comparison. Examination of FIG. 6 shows that the unambiguous decrease in the value of the impedance response from $1.2 \times 10^3$ CFU/ml of stressed E. coli can be detected in as little as 15 minutes with this new method when measuring the initial impedance response, over 10 times faster than with the sensitive impedance monitoring of the growth of un-stressed bacteria. This is to be compared with 14 hours or more for conventional detection methods.

EXAMPLE 3

Impedance Response During the Initial 8 Hours of Growth of E. Coli

Figure 8:
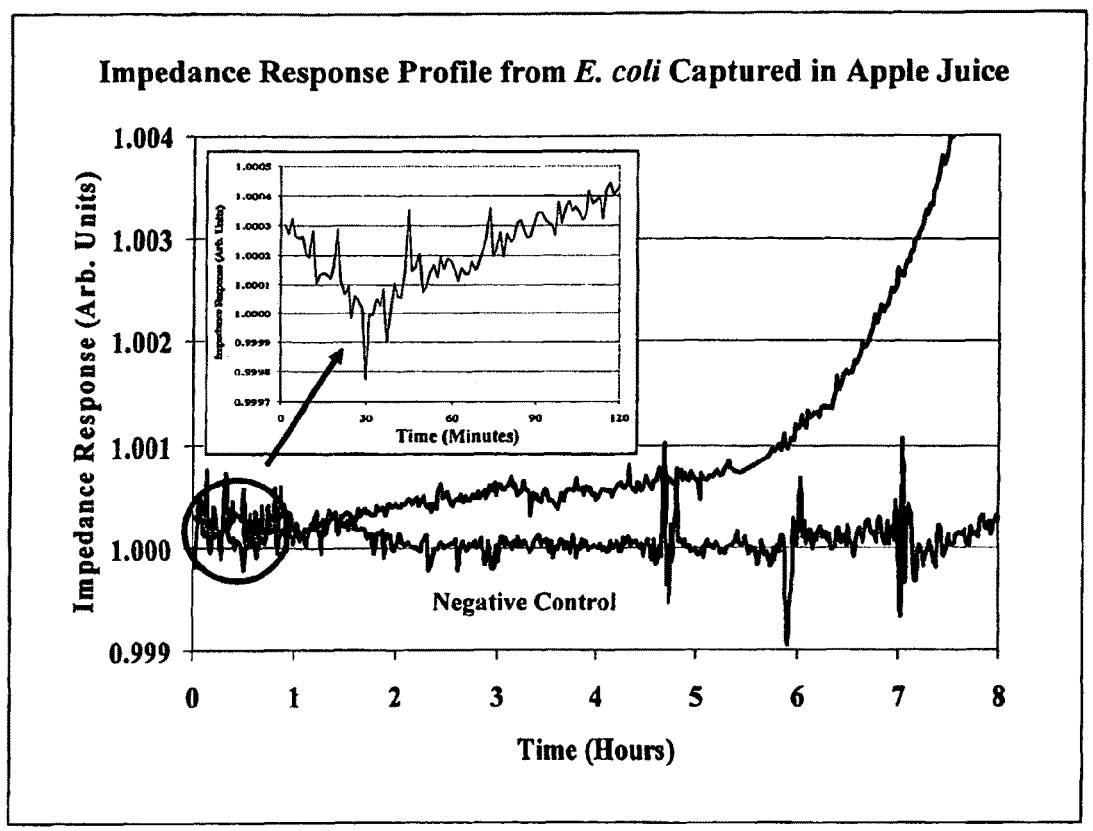
FIG. 8 is a graph representing the impedance response from the growth of 120 CFU/ml *E. coli* over an 8 hour period, and a graph of the impedance of a negative control; and an inset exploded view of the portion of the graph showing the impedance response from *E. coli* during the first 30 minutes of incubation, that is for this example, the initial impedance response.

The impedance response recorded during the initial 8 hours of growth of E. coli (spike ~120 CFU/ml) retrieved from spiked apple juice is plotted in FIG. 8. The initial 120 minutes of the measurement have been expanded and re-plotted as an insert in the same figure. The negative sloping response seen during the first 30 minutes prior to the onset of the well-defined increasing signal is interpreted as biological activity of the viable but not dividing cells experiencing the so called "new medium" stress. In classical microbiology, this period of bacterial growth is called the lag phase or time necessary for bacterial adaptation to new culture conditions. The microbial lag phase is a complex and yet not completely understood phenomenon. We note that 1.) the Impedance Response from stressed cells is similar to that from un-stressed cells during lag phase and 2.) stressed cells returning to optimal growth conditions show longer lag phases.

Based on these two observations we interpret the lag phase seen in FIG. 8 as being metabolically equivalent to mild stress conditions. Thus, with an initial cell concentration as low as only 120 CFU/ml, a mild stress response from environmental change alone produced a detectable decrease in the value of the impedance response sufficiently strong to identify the presence of viable cells in less than 30 minutes, thus demonstrating the sensitivity of the method.

EXAMPLE 4

Detection of E. Coli In Urine

Figure 9:
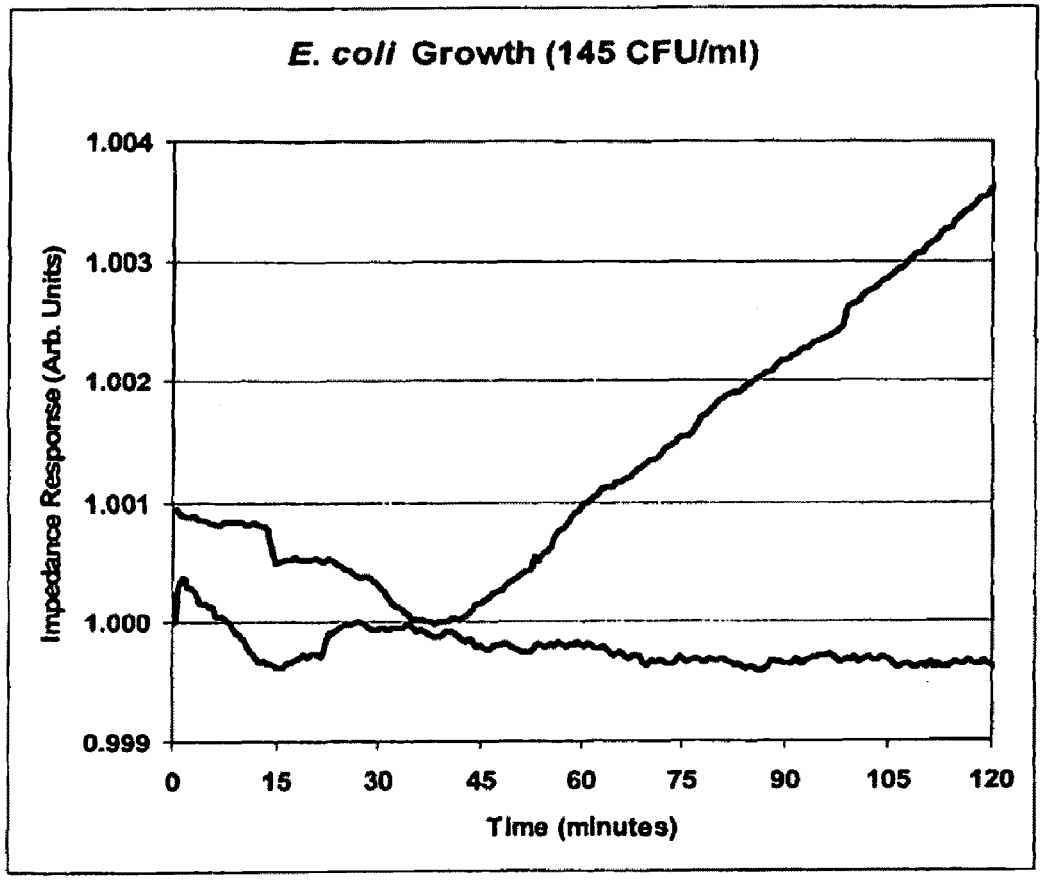
FIG. 9 is a graph representing the impedance response from 145 CFU/ml *E. coli* grown in a 1:1 mixture of urine and tryptic soy broth (TSB) medium.
Figure 10:
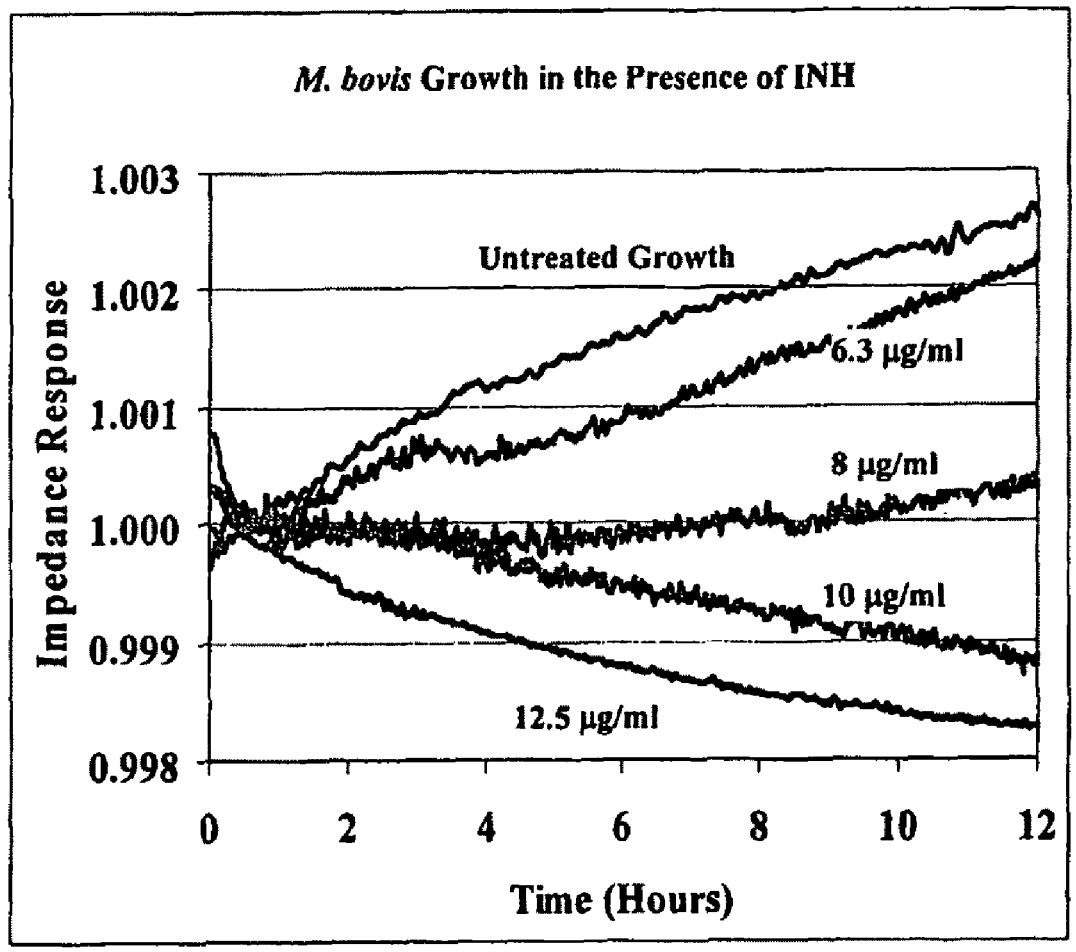
FIG. 10 is a graph representing the impedance response during metabolic deviations of approximately $5 \times 10^6$ CFU/ml *Mycobacterium bovis* (*M. bovis*) after exposure to varying concentrations of isoniazid (INH), all responses scaled to equal 1.000 at the start.
Figure 11:
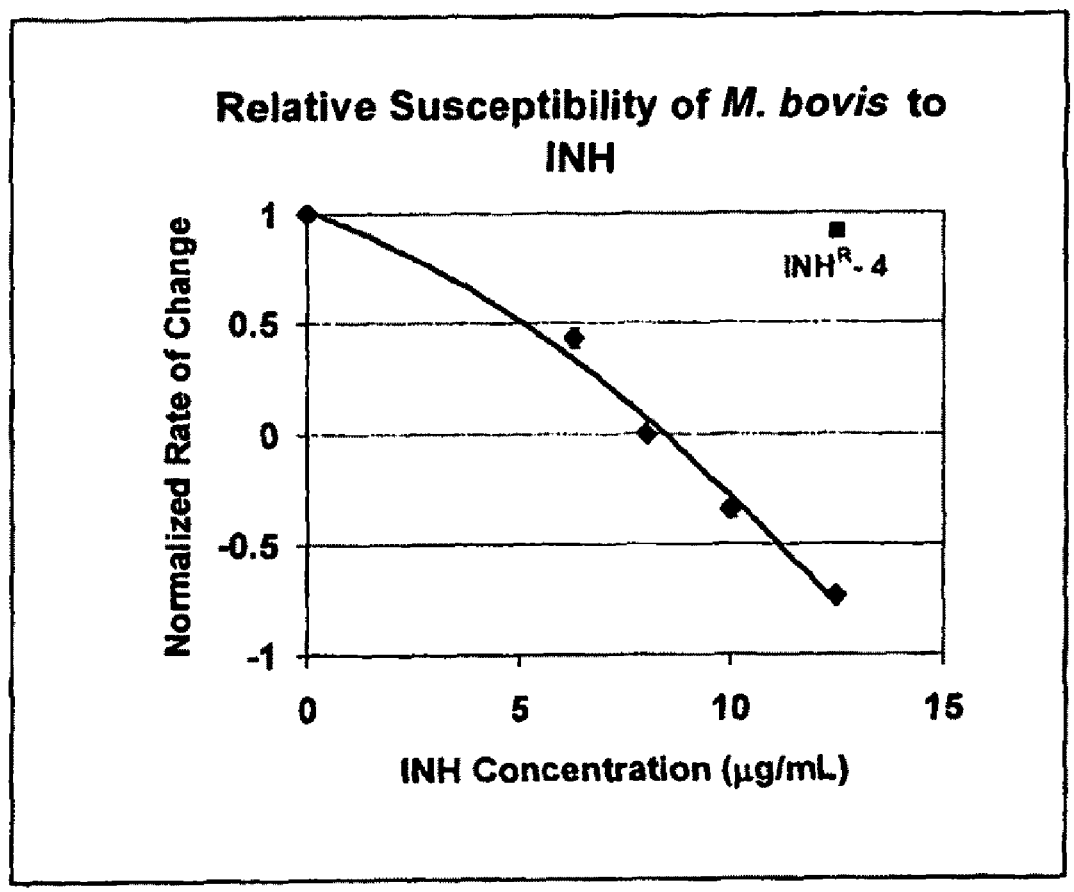
FIG. 11 is a graph representing the susceptibility of *M. bovis*, wherein after four hours growth, the slopes of the corresponding viability curves (FIG. 10) were determined and normalized to the growth of untreated *M. bovis*, and plotted against their respective drug concentration; the similarly normalized slope for the resistant mutant $INH^R$-4 is plotted as a square in the upper right corner.

As an additional example of the sensitivity of the method, an inoculum of 145 CFU/ml of E. coli in a 1:1 V/V mixture of urine and TSB medium suspension was monitored in one chamber along with the medium-urine mixture only in the other. The Impedance Response Profile, which is the calculated ratio of the respective two capacitive components of the impedance signals, is plotted in FIG. 9 along with a negative control (urine/medium only in both chambers) and characterizes the lag phase and subsequent growth occurring within the bacterial suspension.

The "initial impedance response" comprises the decrease in the value of the impedance response profile that is observed during the initial 45 minutes of the measure and is detectable well before then. The onset of the well-defined increase in the impedance response profile corresponds to growth. The inflection point at 45 minutes where the slope of the impedance response profile changes from a negative slope to a positive slope corresponds to the end of the stress response and the beginning of the growth in population. The initial impedance response reflects a mild stress response of the bacterial cells resulting from the environmental stress after transfer into new media (the so-called "new media" stress).

We note that these data correspond to the detection of only 4 bacterial cells (statistical estimate) within the 28.3 microliter (μl) test volume used to generate these data.

Rapid Testing of Susceptibility of a Cell to a Bio-active Agent

In another aspect, the invention provides a method for determining a predictive outcome for the susceptibility of a cell to a selected concentration of a bio-active agent and a level of stress of the cell at the selected concentration of the agent, the method comprising: a) i) at specific time points or over a series of time points, measuring an initial impedance response of a test sample comprising: the cell, a medium, and the selected concentration of the bio-active agent; and measuring an impedance response of a reference sample comprising the medium and the selected concentration of the bio-active agent, wherein said reference sample is devoid of cells; ii) determining a First Impedance Response Treated Profile at each of the time points, wherein the First Impedance Response Treated Profile is a mathematical comparison of the initial impedance response of the test sample determined in step a) (i) and the impedance response of the reference sample determined in step a) (i) at each time point; iii) optionally, repeating steps a) (i) and a) (ii) for a plurality of selected concentrations of the bio-active agent to obtain the corresponding First Impedance Response Treated Profile for each different selected concentration of the known bio-active agent; b) i) at the specific time points or over a series of time points, measuring the initial impedance response of a second test sample comprising the cell and the medium, wherein the second test sample is devoid of the bio-active agent; and measuring the impedance response of a reference sample comprising the medium, wherein said reference sample is devoid of cells; ii) calculating a First Impedance Response Untreated Profile, wherein the First Impedance Response Untreated Profile is a mathematical comparison of the initial impedance response of the second test sample determined in step b) i) and the impedance response of the reference sample determined in step b) i) at each time point; c) for each selected concentration of the bio-active agent, determining a Normalized Impedance Response value, NIR, wherein the NIR is a numerical value determined by an algorithm relating the First Impedance Response Treated Profile value obtained in step a) ii), and/or step a) iii), to the First Impedance Response Untreated Profile value obtained in step b) ii), such that the First Impedance Response Untreated Profile value is incorporated in the NIR, and wherein the determined NIR value is a quantitative measure of the level of stress of the cell at the selected concentration of the bio-active agent.

An embodiment of the above-described method can further be characterized as follows: The mathematical comparison in step a) ii) of the initial impedance response of the test sample determined in step a) (i) and the impedance response of the reference sample determined in step a) (i) at each time point is chosen from: a ratio of the impedance response of the test sample determined in step a) i) and the impedance response of the reference sample determined in step a) i) at each time point, and a difference between the impedance response of the test sample determined in step a) i) and the impedance response of the reference sample determined in step a) i) at each time point.

Further, in an embodiment of the above invention, the algorithm used to determine the NIR is chosen from a mathematical ratio or an absolute difference between the First Impedance Response Treated Profile value and the First Impedance Response Untreated Profile value.

In yet another aspect of the method of determining susceptibility to a bio-active agent, wherein the cell is previously known to be susceptible to the bio-active agent, the method further comprises: repeating steps a), b), and c) with a second cell having an unknown susceptibility to the bio-active agent, wherein the second cell is of the same type as the cell previously known to be susceptible to the bio-active agent, thereby determining the Normalized Impedance Response value, $NIR_{UNK}$, for the cell having unknown susceptibility to the bio-active agent; comparing the $NIR_{UNK}$ value at the selected concentration, for the cell having unknown susceptibility to the bio-active agent, to the NIR value at the selected concentration for the cell of the strain previously known to be susceptible to the bio-active agent; and if the $NIR_{UNK}$ value at the selected concentration is greater than the NIR value at the selected concentration for the cell previously known to be susceptible to the bio-active agent, then predicting that the cell having unknown susceptibility to the bio-active agent is less susceptible to the bio-active agent at the selected concentration, than the cell previously known to be susceptible to the bio-active agent.

In yet another aspect of the method of determining susceptibility to a bio-active agent, wherein the cell is of a strain known or determined to be susceptible to the bio-active agent, the method further comprises: for the specific time points or for the series of time points, plotting, as a function of time, the First Impedance Response Treated Profile for each different selected concentration of the bio-active agent, and the First Impedance Response Untreated Profile of the second test sample comprising the cell and the medium, wherein the second test sample is devoid of the bio-active agent, thereby obtaining a family of curves for the selected concentrations of the bio-active agent and for the untreated cell; calculating an average slope of each curve at a selected time point; obtaining a normalized slope value for each First Impedance Response Treated Profile by dividing the value of the average slope of each curve at the selected time point by the value of the slope of the First Impedance Response Untreated Profile curve; or by otherwise modifying the value of the average slope of each curve at the selected time point by the value of the slope of the First Impedance Response Untreated Profile curve; plotting the normalized slope of each First Impedance Response Treated Profile as a function of the corresponding concentration of the bio-active agent, thereby obtaining a Normalized Rate of Change Curve that can be used to predict an effective concentration of the bio-active agent for the cell; determining the normalized slope value for an unknown cell strain, wherein if the normalized slope value for the unknown cell strain lies above the Normalized Rate of Change Curve of the cell strain known to be susceptible to the bio-active agent; then determining that the unknown cell strain is resistant to the bio-active agent, as determined by other methods.

A non-limiting example of rapid drug susceptibility testing follows.

EXAMPLE 4

Measurement of Rapid Drug Susceptibility Testing

As previously stated, culturing infectious samples is currently time consuming because of the time required for observable growth of the biological constituents to occur, the major obstacle in rapid drug resistance testing. Instead of relying on growth, the described impedance-based method overcomes this obstacle to determine the drug susceptibility of culturable and viable but non-culturable organisms rapidly by monitoring the microorganism's corresponding initial impedance response to the applied stress during exposure to antimicrobial compounds. Impedance data for susceptible and resistant strains of the slow-growing bacterium Mycobacterium bovis BCG (*M. bovis*) exposed to isoniazid (INH) (Sigma-Aldrich, St. Louis, Mo.) are introduced as a demonstration of the method.

These data show that drug susceptibility results normally requiring many weeks using standard plating methods, can be obtained in as little as four hours time. In these experiments a starting inoculum of $5\times10^6$ CFU/ml of M bovis cells suspended in 7H9T broth (Becton Dickinson Microbiology Systems, Sparks, Md.) was mixed with a predetermined concentration of INH and injected into one chamber of the cassette. In the adjacent chamber a mixture of the identical broth with the appropriate concentration of the drug but without cells was injected and was used as the reference.

Impedance Response profiles obtained from the target and reference capacitance signals for five INH drug concentrations (0 to 12.5 μg/ml) were obtained and are plotted in FIG. 10. Each profile infers the stress response from the sensitive M bovis strain and shows that the organism's stress response varies with the drug concentration and reflects its susceptibility to the drug.

All responses have been scaled to equal 1.000 at the start. A family of curves is seen unambiguously differentiating changes in the stress response of the cell as a function of drug concentration for the compound.

Analysis of Example 4

Each point on these curves represents the value of the capacitance signal of the cell-medium-drug suspension divided by that of the medium-drug mixture at the different measurement times. Because these data are constructed as ratios, the reference (control) measurement is automatically incorporated and the effects from background are minimized. Overall, the slope of the Impedance Response Profile decreases as the drug concentration is increased indicating a more significant stress response and corresponding reduction in cell viability when compared with the growth. This trend was confirmed by corresponding plate counts obtained at the end of each experiment.

Measurement of Drug Resistance. A spontaneous mutant of *M. bovis* resistant to INH was isolated and characterized. This was accomplished by isolating mutant colonies from a 7H10 drug plate containing gradient concentrations of INH ranging from 0 to 63 μg INH/ml (equivalent to 0-10× minimum inhibitory concentration (MIC) of the sensitive strain) followed by subsequent re-culturing on a second fresh 7H10 agar drug plate having a 25 μg/ml (4×MIC) concentration of INH. The drug susceptibility of this mutant was quantified using standard micro-broth dilution method and the corresponding MIC for $INH^R$-4, the mutant selected for the impedance measurements, had a value of approximately 50 μg/ml (8×MIC of the sensitive strain) confirming its resistance.

The impedance responses from the resistant mutant grown in the presence or absence of a drug (12.5 μg/ml INH (2×MIC)) versus a control (medium containing no cells) were obtained. These measured impedance responses were identical to each other and also similar to that of the sensitive strain grown without a drug as shown in FIG. 10. In addition, the curves are qualitatively distinct from the flat response of a negative control containing no cells.

Impedance Response Correlations with Drug Concentration. The different impedance responses plotted in FIG. 10 can be presented in a succinct form amenable to easy interpretation. Drug concentration-impedance response correlations are revealed by calculating a relative rate of change at a single fixed time point and plotting the result as a function of the corresponding drug concentration. For these data, the value of the impedance response for each curve was obtained at only four hours, a fraction of the population doubling time for this species and well before bacterial growth may start. The average slope was calculated using that value and the common starting value (i.e, Impedance Response=1.000 Arbitrary Units).

Next, the respective values of these slopes were divided by the value from the growth data to obtain "normalized" values. These final values are plotted against the drug concentration in FIG. 11. These "normalized" data points are part of a locust of points (indicated by the curve) quantifying the microorganism's stress response to the drug and are a representation of its susceptibility. Specifically, the locus of points plotted in FIG. 11 describe the stress response of the sensitive *M. bovis* strain (determined a priori using conventional methods) to the drug INH and serves as the basis for a predictive measure for determining the susceptibility of the cells to an antimicrobial compound. For a given drug concentration, a different *M. bovis* strain having a measured normalized value lying above the corresponding point on the locus of points representing the stress response from a susceptible cell would indicate drug resistance; similarly, a point below the standard would indicate enhanced sensitivity.

For example, since the impedance responses measured for the resistant mutant in the presence and absence of INH are the same, the "normalized" value of the slope equals one indicating that exposure to 12.5 μg/ml of INH has no affect on the viability of the resistant mutant—consistent with its measured susceptibility threshold of 8×MIC. The normalized slope value for the resistant strain, $INH^R$-4, (FIG. 11—square at top right) is seen far outside of the data trend for the sensitive strain identifying it as highly resistant to INH.

Stress and Susceptibility. Drug susceptibility information is normally obtained from multiple drug dilution measurements via numerous single-point growth experiments or by means of a diffusion gradient. The method described here extracts this same information from multiple measurements over time but using a single drug concentration. The data plotted in FIG. 11 demonstrate a one-to-one relationship between drug concentration and the impedance derived parameter. Thus, calculation of this derived parameter from a measured time series data when plotted versus the actual drug concentration used represents the corresponding stress level inferring the susceptibility of the cell to the drug. This is accomplished by developing an algorithm and the compilation of a database for different cells and drugs.

To summarize, the respective impedance responses for the different organism/drug concentration combinations measured were plotted together as a family of curves (FIG. 10) fully mapping out the corresponding stress responses of the treated organism. An efficient analytical parameterization was created and applied to produce these dose-viability curves (FIG. 11). The parameterization used is relative to the growth of untreated cells (obtained simultaneously) to ensure that all measurements are internally controlled.

Detection of Microorganisms In Complex Samples

EXAMPLE 5

Detection of Bacteria In Blood

To demonstrate the effectiveness of the method in complex sample matrices, human platelet concentrates (PC) were spiked with different species of bacteria and subjected to detection using the BioSense impedance platform. Additional consideration must be taken when working with complex samples. For example, in the case of blood, platelets, residual white blood cells (WBCs), and red blood cells (RBCs) are metabolically active and consume oxygen and/or glucose and may interfere with the impedance measurement of the bacterial stress response. Thus, their presence must be minimized to ensure a sensitive measurement. In addition, bacteria embedded in blood and/or other cells or adhering to their surface must be liberated to ensure that all bacteria are detected and false negative results do not occur.

In the following example, advantage is taken of the fragility of the platelets and other human blood cells as compared to any contaminant bacteria. Prior to impedance sensing, a mild detergent was added to the PC sample lysing all blood cells while simultaneously inducing metabolic stress in any contaminant bacteria. The former eliminates any potential interference from metabolically active human cells that could contribute unwanted signal; the latter provides a measurable impedance response identifying presence of viable bacteria in the sample by their specific stress response. Once lysis was complete, the suspension was passed through filters designed to pass and obstruct bacteria for the target and reference samples, respectively.

This protocol addresses all of the essential considerations for a practical assay. For example, the pass-through efficiency of filtering *S. epidermidis* after lysis was measured to be nearly 100 percent with our protocol. For comparison, Ortolando et al. measured the transmission of *S. epidermidis* after filtering similar but unlysed leukocyte-reduced platelet concentrates to be only approximately 50 percent indicating the effectiveness and advantage of our approach.

Spiked PC Experiments. Fresh units of PC were spiked with our model bacteria, stressed and filtered, and the respective Impedance Responses were measured. Fresh units of PC were obtained and 2 ml sample was subjected to lysis with PBS added instead of bacterial spike. The lysate was then diluted with BHI (1:1 V/V), passed through a 5 µm syringe filter to sift out large fragments and possible platelet aggregates but not bacteria. A portion of this filtrate was passed through a 0.2 µm syringe filter to remove all bacterial cells. The two cassette detection chambers were filled with the respective samples and the capacitance signals were recorded. The flat baseline Impedance Response from the PC lysates containing no bacteria is plotted in FIG. 12 (red curve labeled "Negative Control"). The minor increase in impedance response seen during the first 5 minutes is attributed to thermal differences between the two chambers.

The remainder of the PC was used for spiking with the model bacteria. In each case, spikes on the order of $10^3$ CFU/ml were obtained. Immediately after the spike, the described lysis/filtration protocol was applied and the cassette detection chambers were filled. The cassette was inserted into the temperature controlled analyzer, the capacitances of the two chambers were recorded, and the Impedance Response was calculated. Starting and ending bacterial cell numbers were enumerated using standard plating methods and CFUs were consistent with no statistically significant loss in titers or viability.

Figure 12A:
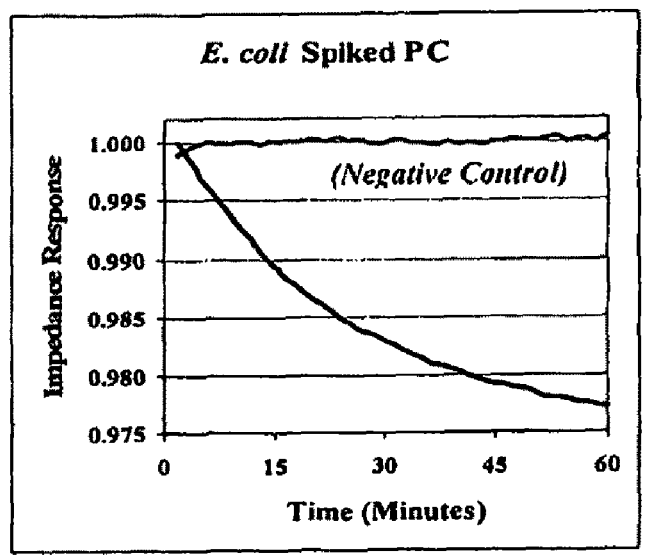
FIG. 12A, FIG. 12B, and FIG. 12C are graphs representing the impedance responses, respectively, from platelet concentrates (PC) spiked with *E. coli* ($4.0 \times 10^3$ CFU/ml); *Staphylococcus epidermidis* ($3.2 \times 10^3$ CFU/ml); *Propionibacterium acnes* ($2.8 \times 10^3$ CFU/ml), along with negative control graph.
Figure 12B:
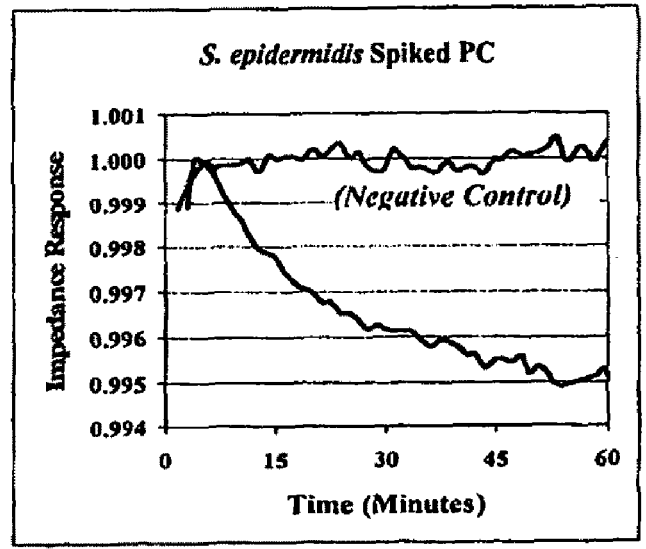
Figure 12C:
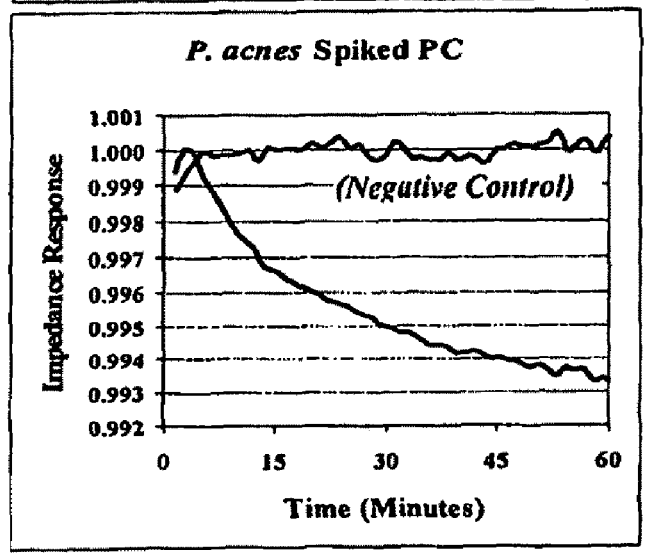

The initial impedance responses for Gram-negative *Escherichia coli* ($4\times10^3$ CFU/ml), Gram-positive *Staphylococcus epidermidis* ($3.2\times10^3$ CFU/ml), and the slow growing Gram-positive anaerobe *Propionibacterium acnes* ($2.8\times10^3$ CFU/ml) are plotted together with the same negative control in FIG. 12A, FIG. 12B, and FIG. 12C, respectively. The measured values of the impedance response from all three bacteria exposed to the stressor clearly differ from the flat impedance response of the negative control data and continuously decrease in value establishing an unambiguous trend easily detected within 15 minutes.

The brief increase in the *S. epidermis* and *P. acnes* responses before the onset of the decrease is attributed again to thermal differences prior to equilibrium and is evident because the signals sizes are quantitatively closer in scale with that from the negative control compared to the response from highly stressed *E. coli*. It is important to note that since *E. coli* is highly susceptible to poor survival in plasma, a culture sequentially cycled three times in different platelets was isolated and used to ensure adapted survival of this bacterium in PC.

The following observations are drawn from a comparison of the data from all three organisms:

The Impedance Responses for all three bacterial species are qualitatively similar, decreasing in value, and well-differentiated from the flat response of the negative control (un-spiked PC supernatant).

The Impedance Response from stressed microorganisms in a complex sample is qualitatively similar to that from stressed microorganisms in conventional media.

The method works equally well when detecting anaerobic bacteria (*P. acnes*) as when detecting aerobic (*S. epidermidis*) or facultative anaerobic (*E. coli*) species.

All responses are immediate providing definitive results between 10 and 30 minutes irrespective of the actual doubling time of the microorganism underlining that our method of detection is a truly rapid method.

The Impedance Responses from the three different bacteria are quantitatively different. We suggest that these differences result from i.) diverse metabolic responses from the different species, ii.) varying bacterial cell numbers, iii) different sensitivity to stressor used in the study, and iv.) cassette to cassette mechanical variations resulting in different signal gain.

Disclosed herein are various kits to facilitate carrying out the methodology according to various embodiments. One embodiment of a disclosed kit is useful for rapidly detecting, according to the disclosed method, the presence or absence of a cell in a test sample of a medium. The kit comprises: at least one stressor previously known to cause a stress response in the cell, if the cell is present in the test sample; and a set of directions for using the components of the kit according to the method of claim 6 for detecting the presence or absence of the cell in the test sample.

Another disclosed kit is described for determining the presence or absence of a viable cell within a test sample. The kit comprises: a) a medium from which a suspension of a test sample and a stressor can be prepared for testing; and b) a set of directions for using the components of the kit according to the disclosed method of claim 14 for determining the level of the initial impedance response of the test sample and stressor, a predictive outcome for the viability of the cell, and a level of stress of the cell at the selected concentration of the bio-active agent.

Yet another disclosed kit facilitates the determination, according a disclosed method, of the susceptibility of a cell to a selected concentration of a bio-active agent and a level of stress of the cell at the selected concentration of the bio-active agent. The kit for determining susceptibility comprises: a) a medium from which a suspension of a test sample of the cell and a suspension of each concentration of the bio-active agent can be prepared for testing; and b) a set of directions for using the components of the kit according to a disclosed method, and to determine a level of stress of the cell at the selected concentration of the bio-active agent.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for rapidly monitoring a stress response of cells suspended in a medium to a stressor comprising:
   a) under conditions suitable for monitoring the voltage and/or the current, applying an electric field generated by at least one specified frequency to a test sample comprising the cells suspended in the medium or to a test sample comprising the cells on suspended micro culture beads;
   b) monitoring the voltage and/or the current;
   c) applying a stressor to the test sample, wherein the time of applying the stressor is chosen from prior to, substantially simultaneously with, and subsequent to the time of applying the electric field;
   d) determining:
      (i) the impedance response of the test sample for a time period either from the time of initially applying the electric field or from the time of applying the stressor, whichever is later, up to 45 minutes after the time of the application of the electric field or the time of the application of the stressor, whichever is later;
      (ii) a first standard value which is the impedance response of a first reference sample comprising said medium with or without the stressor, wherein the first reference sample is devoid of cells; and/or
      (iii) a second standard value which is the impedance response of a second reference sample comprising the cells and the medium, wherein the cells in the second reference sample are of the same type and concentration as the cells in the test sample, and wherein the second reference sample is devoid of the stressor;
   wherein said first standard value and said second standard value are determined under the same conditions and during the same time period as that of said test sample;
   wherein any change in the impedance response of the test sample compared with said first standard value and/or said second standard value is indicative of the stress response of said cells to the stressor.

2. The method of claim 1 further comprising:
   e) mathematically determining the amount of change of the impedance response of the test sample with said first standard value and/or said second standard value determined in step d),
   wherein said amount of change of the impedance response of the test sample is an indication of the magnitude of the stress response of the cells to said stressor.

3. The method of claim 1, wherein the cells suspended in a medium are chosen from a prokaryotic cell type and a eukaryotic cell type.

4. The method of claim 1, wherein the stressor applied to the cells suspended in a medium comprises contacting the cells suspended in the medium with a known bio-active agent.

5. The method of claim 1, wherein the known bio-active agent is chosen from a pharmaceutically active agent, an anti-cancer agent, a biological toxin, a virus, another substance capable of producing stress, and combinations thereof.

6. A method for rapidly detecting the presence of viable cells by monitoring a stress response of the viable cells if said viable cells are present, or the absence of a stress response if said cells are absent or dead, comprising:
   a) under conditions suitable for monitoring the voltage and/or the current, applying an electric field generated by at least one specified frequency to a test sample comprising the cells, if present, suspended in a medium or to a test sample comprising the cells, if present, on suspended micro culture beads;
   b) monitoring the voltage and/or the current;
   c) applying a stressor to the test sample, wherein the time of applying the stressor is chosen from prior to, substantially simultaneously with, or subsequent to the time of applying the electric field;
   d) at a specific time point or over a series of time points,
      (i) measuring the impedance response of the test sample for a time period either from the time of initially applying the electric field or from the time of applying the stressor, whichever is later, up to 45 minutes after the time of the application of the electric field or the time of the application of the stressor, whichever is later;
      (ii) determining a first standard value which is the impedance response of a first reference sample comprising the medium with or without the stressor, wherein the first reference sample is devoid of cells; and/or
      (iii) determining a second standard value which is the impedance response of a second reference sample comprising said cells and the medium, wherein the cells in the second reference sample are of the assumed same type and concentration as the cells in the test sample, and wherein the second reference sample is devoid of the stressor;
   wherein said first standard value and said second standard value are determined under the same conditions and during the same time period as that of said test sample;
   wherein any change in the impedance response of the test sample compared with said first standard value and/or said second standard value is indicative of the stress response of said viable cells to the stressor, and wherein no change in the impedance response of the test sample compared with said first standard value and/or said second standard value is indicative that said cells are either absent from the test sample or dead;
   thereby rapidly detecting the presence or absence of said viable cells in the test sample.

7. The method of claim 6 further confirming the presence or absence of said viable cells in the test sample comprising:
   e) mathematically determining the amount of change of the impedance response of the test sample with said first standard value and/or said second standard value at said specific time point or series of time points in step d),
   wherein said amount of change(s), if any, are an indication of the magnitude of the stress responses of the viable cells to the stressor, and wherein no change(s) are an indication that said cells are either absent or dead;
   thereby confirming the presence or absence of said viable cells in the test sample.

8. The method of claim 6, wherein the cells suspended in a medium are chosen from a prokaryotic cell type and a eukaryotic cell type.

9. The method of claim 8, wherein the cells suspended in a medium are a eukaryotic cell type chosen from protists, fungi, a non-transformed human cell, a non-transformed animal cell, a transformed human cell, and a transformed animal cell, with the proviso that if the eukaryotic cell type is adhesion-dependent, the test sample medium additionally comprises suspended micro culture beads comprising a coating of an extracellular matrix capable of adhering to the eukaryotic cell type.

10. The method of claim 8, wherein the cells suspended in a medium are a prokaryotic cell type or eukaryotic cell type, and the test sample medium and the reference sample medium additionally comprise suspended beads comprising a coating of specific receptors capable of adhering to the prokaryotic or eukaryotic cells.

11. The method of claim 10, wherein the receptors comprise biologically active components chosen from components generated from immunological responses, components generated from nucleic acids, and components generated from other chemical compounds that can be used to identify specific cells.

12. The method of claim 6, wherein the stressor applied to the cells suspended in a medium comprises contacting the cells suspended in the medium with a known bio-active agent.

13. The method of claim 12, wherein the known bio-active agent is chosen from a pharmaceutically active agent, an anti-cancer agent, a biological toxin, a virus, another substance capable of producing stress, and combinations thereof.

14. A method for determining a predictive outcome for the susceptibility of cells suspended in a medium to a selected concentration of a bio-active agent and the amount of stress of the cells at the selected concentration of the bio-active agent, wherein the susceptibility and amount of stress of the cells to said bio-active agent is previously known or unknown, comprising:
   a) under conditions suitable for monitoring the voltage and/or the current, applying an electric field generated by at least one specified frequency to a test sample comprising the cells suspended in a medium or to a test sample comprising the cells on suspended micro culture beads;
   b) monitoring the voltage and/or the current;
   c) applying the bio-active agent to the test sample, wherein the time of applying the bio-active agent is chosen from prior to, substantially simultaneously with, or subsequent to the time of applying the electric field;
   d) at a specific time point or over a series of time points,
      (i) measuring an impedance response of a test sample comprising the cells suspended in the medium or suspended on micro culture beads, and the selected concentration of the bio-active agent for a time period either from the time of initially applying the electric field or from the time of applying the bio-active agent, whichever is later, up to 45 minutes after the time of the application of the electric field or the time of the application of the bio-active agent, whichever is later;
      (ii) measuring an impedance response of a reference sample comprising the medium and the selected concentration of the bio-active agent, wherein said reference sample is devoid of cells but contains the bio-active agent, and wherein said impedance response of the reference sample is determined under the same conditions and during the same time period as that of said test sample;
      (iii) calculating a First Impedance Response Treated Profile at each of the time points, wherein the First Impedance Response Treated Profile is a mathematical comparison of the impedance response of the test sample determined in step d)(i) and the impedance response of the reference sample determined in step d)(ii) at each time point;
      (iv) optionally, repeating steps d)(i) and d)(ii) for a plurality of selected concentrations of the bio-active agent to obtain the corresponding First Impedance Response Treated Profile for each different selected concentration of the known bio-active agent;
   e) at the same specific time point or over the same series of time points as in step d),
      (i) measuring the impedance response of a second test sample comprising said cells suspended in the medium or on micro culture beads, wherein the second test sample is devoid of the bio-active agent, for a time period either from the time of initially applying the electric field or from the time of applying the bio-active agent, whichever is later, up to 45 minutes after the time of the application of the electric field or the time of the application of the bio-active agent, whichever is later;
      (ii) measuring the impedance response of a second reference sample comprising said cells suspended in the medium or on suspended micro culture beads, wherein said second reference sample is devoid of cells and devoid of the bio-active agent, and wherein said impedance response of said second reference sample is determined under the same conditions and during the same time period as that of said second test sample;
      (iii) calculating a First Impedance Response Untreated Profile, wherein the First Impedance Response Untreated Profile is a mathematical comparison of the impedance response of the second test sample determined in step e)(i) and the impedance response of the second reference sample determined in step e)(ii) at each time point;
      (iv) repeating steps e)(i) and e)(ii) for the same plurality of selected concentrations of the bio-active agent, if any, as used in step d)(iv) to obtain the corresponding First Impedance Response Untreated Profile for each different selected concentration of the known bio-active agent; and
   f) for each selected concentration of the bio-active agent, determining a Normalized Impedance Response value, NIR, wherein the NIR is a numerical value determined by an algorithm relating the First Impedance Response Treated Profile value obtained in step d)(iii), and/or step d)(iv), to the First Impedance Response Untreated Profile value obtained in step e)(iii) and/or step e)(iv), wherein the determined NIR is an indication of the susceptibility and a quantitative measure of the amount of stress of the cells at each selected concentration of the bio-active agent.

15. The method of claim 14, wherein the mathematical comparison in step d)(iii) of the impedance response of the test sample determined in step d)(i) and the impedance response of the reference sample determined in step d)(ii) at each time point is chosen from:
   a ratio of the impedance response of the test sample determined in step d)(i) and the impedance response of the reference sample determined in step d)(ii) at each time point, and
   a difference between the impedance response of the test sample determined in step d)(i) and the impedance response of the reference sample determined in step d)(ii) at each time point; and wherein the mathematical comparison in step e)(iii) of the impedance response of the test sample determined in step e)(i) and the impedance response of the reference sample determined in step e)(ii) at each time point is chosen from:
   a ratio of the impedance response of the test sample determined in step e)(i) and the impedance response of the reference sample determined in step e)(ii) at each time point, and a difference between the impedance response of the test sample determined in step e)(i) and the impedance response of the reference sample determined in step e)(ii) at each time point;

provided that when said ratio of impedance responses is used as the mathematical comparison in step d)(iii), said ratio of impedance responses is used as the mathematical comparison in step e)(iii), and when said difference of impedance responses is used as the mathematical comparison in step d)(iii), said difference of impedance responses is used as the mathematical comparison in step e)(iii).

16. The method of claim 14, wherein the algorithm used to determine the NIR is chosen from a mathematical ratio and an absolute difference between the First Impedance Response Treated Profile and the First Impedance Response Untreated Profile.

17. The method of claim 14, wherein said cells are previously known to be susceptible to the bio-active agent, further comprising:

g) repeating steps a) through with a second group of cells having an unknown susceptibility to said bio-active agent, wherein the second group of cells are of the same type as said cells previously known to be susceptible to said bio-active agent and the concentrations of the initial cells and the second group of cells are the same, thereby determining the Normalized Impedance Response value, $NIR_{UNK}$, for the group of cells having unknown susceptibility to-said bio-active agent;

wherein for all instances the value for said First Impedance Response Treated Profile calculated in step d)(iii) and/or step d)(iv) is less than the value for said First Impedance Response Untreated Profile calculated in step e)(iii) and/or step e)(iv), and the algorithm for determining both the NIR and the $NIR_{UNK}$ is either, respectively, the ratio of said First Impedance Response Treated Profile to said First Impedance Response Untreated Profile or said First Impedance Response Untreated Profile subtracted from said First Impedance Response Treated Profile;

h) comparing the $NIR_{UNK}$ at each selected concentration of said bio-active agent for the group of cells having unknown susceptibility to said bio-active agent to the NIR at each selected concentration of said bio-active agent for the cells of the strain previously known to be susceptible to said bio-active agent; and when the $NIR_{UNK}$ at each selected concentration is greater than the NIR at each selected concentration for the cells previously known to be susceptible to said bio-active agent, predicting that the cells having unknown susceptibility to said bio-active agent are less susceptible to said bio-active agent at each selected concentration than the cells previously known to be susceptible to said bio-active agent.

18. The method of claim 14, wherein the cells are of a strain known or determined to be susceptible to said bio-active agent, further comprising:

i) for said specific time point or said series of time points of step d), plotting, as a function of time, the First Impedance Response Treated Profile for each different selected concentration of said bio-active agent, wherein said First Impedance Response Treated Profile is the ratio of the impedance response of the test sample determined in step d)(i) to the impedance response of the reference sample determined in step d)(ii), and the First Impedance Response Untreated Profile, wherein said First Impedance Response Untreated Profile is the ratio of the impedance response of the second test sample determined in step e)(i) to the impedance response of the reference sample determined in step e)(ii), thereby obtaining a family of curves for said selected concentrations of said bio-active agent and for each selected time point;

j) measuring the slope of each curve at each selected time point;

k) obtaining a normalized slope value for each First Impedance Response Treated Profile by dividing the value of the slope of each curve at each selected time point by the value of the slope of the First Impedance Response Untreated Profile;

l) plotting the normalized slope values of each First Impedance Response Treated Profile as a function of the corresponding concentration of said bio-active agent, thereby obtaining a Normalized Rate of Change Curve for said cells determined to be susceptible to said bio-active agent;

m) determining a normalized slope value for an unknown cell strain of the same cell species as used in step a) by using steps a) through e) and i) through l) at a selected time point and at a selected concentration of said bio-active agent determined for said susceptible cell strain;

wherein when the normalized slope value for said unknown cell strain lies above the Normalized Rate of Change Curve of said cell strain known to be susceptible to said bio-active agent, the unknown cell strain is resistant to said bio-active agent, and when the normalized slope value for said unknown cell strain lies on or below the Normalized Rate of Change Curve, the unknown cell strain is susceptible to said bio-active agent; and wherein when the normalized slope value for said unknown cell strain lies far above the Normalized Rate of Change Curve of said susceptible cell strain to said bio-active agent, this indicates that the minimum inhibitory concentration, MIC, of said bio-active agent may be many times the MIC of said bio-active agent for said susceptible cell strain.

19. The method of claim 14, wherein the cells are chosen from a prokaryotic cell type and a eukaryotic cell type.

20. The method of claim 19, wherein the cells are a eukaryotic cell type chosen from protists, fungi, a non-transformed human cell type, a non-transformed animal cell type, a transformed human cell type, and a transformed animal cell type, wherein if the eukaryotic cell type is adhesion-dependent, the test sample medium additionally comprises suspended micro culture beads with a coating of an extracellular matrix capable of adhering to said eukaryotic cell type.

21. The method of claim 19, wherein the cells are a prokaryotic cell type or eukaryotic cell type, and the test sample medium and the reference sample medium additionally comprise suspended beads with a coating of specific receptors capable of adhering to the prokaryotic or eukaryotic cells.

22. The method of claim 21, wherein the receptors comprise biologically active components chosen from components generated from immunological responses, components generated from nucleic acids, and components generated from other chemical compounds that can be used to identify said cells.

* * * * *